(12) United States Patent
Bacus et al.

(10) Patent No.: US 6,674,884 B2
(45) Date of Patent: Jan. 6, 2004

(54) APPARATUS FOR REMOTE CONTROL OF A MICROSCOPE

(75) Inventors: James V. Bacus, Downers Grove, IL (US); James W. Bacus, Oakbrook, IL (US)

(73) Assignee: Bacus Laboratories, Inc., Lombard, IL (US)

( * ) Notice: Subject to any disclaimer, the term of this patent is extended or adjusted under 35 U.S.C. 154(b) by 0 days.

(21) Appl. No.: 10/008,519

(22) Filed: Nov. 13, 2001

(65) Prior Publication Data

US 2002/0061127 A1 May 23, 2002

Related U.S. Application Data

(63) Continuation of application No. 09/752,022, filed on Dec. 28, 2000, now Pat. No. 6,404,906, which is a division of application No. 09/752,022, which is a division of application No. 09/395,694, filed on Sep. 15, 1999, now Pat. No. 6,226,392, which is a continuation of application No. 08/805,856, filed on Mar. 3, 1997, now Pat. No. 6,101,265, which is a continuation-in-part of application No. 08/701,974, filed on Aug. 24, 1996, now Pat. No. 6,031,930.

(51) Int. Cl.[7] .................................................. G06K 9/00
(52) U.S. Cl. ....................................................... 382/133
(58) Field of Search ................................ 382/128, 129, 382/133; 348/79, 80; 396/432; 359/144, 369, 370, 372, 379, 380, 381, 382, 383; 709/203, 212, 217, 219; 702/19; 725/713

(56) References Cited

U.S. PATENT DOCUMENTS

| | | | |
|---|---|---|---|
| 3,999,047 A | 12/1976 | Green | 382/134 |
| 4,150,360 A | 4/1979 | Kopp et al. | 382/133 |
| 4,175,860 A | 11/1979 | Bacus | 356/39 |

(List continued on next page.)

FOREIGN PATENT DOCUMENTS

| | | | |
|---|---|---|---|
| EP | 0 209 422 | 10/1987 | G06K/11/00 |
| EP | 0 246 010 A | 11/1987 | G06F/15/62 |

(List continued on next page.)

OTHER PUBLICATIONS

*The Cas200™ Automated Pathology Workstation* by James V. Bacus, Compendium on the Computerized Cytology and histology Laboratory, Tutorials of Cytology© 1994.

(List continued on next page.)

*Primary Examiner*—Andrew W. Johns
*Assistant Examiner*—Shervin Nakhjavan
(74) *Attorney, Agent, or Firm*—Fitch, Even, Tabin & Flannery

(57) ABSTRACT

An apparatus and method acquires and stores multiple resolution images from a specimen on a support and provides to the user a low magnification, reconstructed macro image of the entire specimen, or a large portion thereof, to aid the person in selecting points of interest to be viewed or analyzed at higher magnifications and resolution. The reconstructed image is formed of a large number of tiled, stored images which are coordinated and assembled to form the macro image of the specimen which is displayed on a monitor. Preferably, the stored, reconstructed image is reduced further in size by a software system before it is displayed to the user. The display may be on a local monitor over a local area network or sent over the Internet to the user who is typically a pathologist. The user selects by a marker such as a cursor the defined area of interest or region and then views higher magnification images or has them analyzed. Preferably, the pathologist can scroll to shift digitized, adjacent image tiles into view on the monitor. A fully computer-controlled microscope is used to acquire and store the digitized images and the illustrated microscope can be remotely controlled to change objective lenses, focus, light intensity, filters, field diaphragm, and to shift the microscope stage by a controller.

45 Claims, 16 Drawing Sheets

U.S. PATENT DOCUMENTS

| | | | |
|---|---|---|---|
| 4,199,748 A | | 4/1980 | Bacus ........................ 382/134 |
| 4,213,036 A | | 7/1980 | Kopp et al. .................. 382/133 |
| 4,523,278 A | | 6/1985 | Reinhardt et al. ........... 382/133 |
| 4,742,558 A | | 5/1988 | Ishibashi et al. ............. 382/240 |
| 4,760,385 A | | 7/1988 | Jansson ...................... 345/641 |
| 4,777,525 A | * | 10/1988 | Preston, Jr. ................. 348/111 |
| 4,887,892 A | | 12/1989 | Bacus ........................ 382/133 |
| 4,965,725 A | * | 10/1990 | Rutenberg .................. 382/224 |
| 5,018,209 A | | 5/1991 | Bacus ........................ 382/129 |
| 5,068,906 A | | 11/1991 | Kosaka ....................... 382/133 |
| 5,072,382 A | | 12/1991 | Kamentsky ................. 382/133 |
| 5,073,857 A | | 12/1991 | Peters et al. ................. 382/133 |
| 5,099,521 A | | 3/1992 | Kosaka ....................... 382/133 |
| 5,107,422 A | | 4/1992 | Kamentsky et al. ......... 382/133 |
| 5,123,056 A | | 6/1992 | Wilson ....................... 382/132 |
| 5,163,095 A | | 11/1992 | Kosaka ....................... 382/133 |
| 5,216,500 A | | 6/1993 | Krummey et al. ............ 348/79 |
| 5,216,596 A | | 6/1993 | Weinstein .................... 348/79 |
| 5,218,645 A | | 6/1993 | Bacus ........................ 382/133 |
| 5,252,487 A | | 10/1993 | Bacus et al. .................. 436/63 |
| 5,257,182 A | | 10/1993 | Luck et al. .................. 382/224 |
| 5,260,871 A | | 11/1993 | Goldberg ................... 600/320 |
| 5,268,966 A | | 12/1993 | Kasdan ...................... 382/133 |
| 5,287,272 A | | 2/1994 | Rutenberg et al. .......... 382/224 |
| 5,297,034 A | | 3/1994 | Weinstein ................... 382/128 |
| 5,313,532 A | | 5/1994 | Harvey et al. ............... 382/156 |
| 5,333,207 A | | 7/1994 | Rutenberg .................. 382/133 |
| 5,428,690 A | | 6/1995 | Bacus et al. ................. 382/128 |
| 5,473,706 A | | 12/1995 | Bacus et al. ................. 382/133 |
| 5,499,097 A | | 3/1996 | Ortyn et al. ................. 356/615 |
| 5,505,946 A | | 4/1996 | Kennedy et al. ............ 424/757 |
| 5,544,650 A | | 8/1996 | Boon et al. .................. 600/309 |
| 5,625,765 A | | 4/1997 | Ellenby et al. .............. 345/633 |
| 5,655,029 A | * | 8/1997 | Rutenburg et al. .......... 382/133 |
| 5,784,162 A | | 7/1998 | Cabib et al. ................. 356/456 |
| 5,793,969 A | | 8/1998 | Kamentsky et al. ......... 709/213 |
| 5,796,861 A | | 8/1998 | Vogt et al. .................. 382/128 |
| 5,836,877 A | | 11/1998 | Zavislan .................... 600/407 |
| 5,838,837 A | | 11/1998 | Hirosawa et al. ........... 382/284 |
| 5,978,804 A | | 11/1999 | Dietzman .................... 707/10 |
| 5,993,001 A | | 11/1999 | Bursell et al. ............... 351/212 |
| 6,078,681 A | | 6/2000 | Silver ......................... 382/133 |
| 6,091,842 A | | 7/2000 | Domanik et al. ........... 382/133 |
| 6,091,930 A | | 7/2000 | Mortimer et al. ........... 434/362 |
| 6,148,096 A | | 11/2000 | Pressman et al. ........... 382/133 |
| 6,151,405 A | | 11/2000 | Douglass et al. ........... 382/133 |
| 6,430,309 B1 | | 8/2002 | Pressman et al. ........... 382/133 |

FOREIGN PATENT DOCUMENTS

| | | | |
|---|---|---|---|
| JP | 05-313071 | 11/1993 | ........... G02B/21/36 |
| JP | 06-118307 | 4/1994 | ........... G02B/21/26 |
| JP | 07-015712 | 1/1995 | ........... H04N/7/18 |

OTHER PUBLICATIONS

Szeliski R: "Image Mosiaicing for Tele–Reality Applications" Proceedings of the IEEE Workshop on Applications of Computer Vision, XX, XX, May 1, 1994, pp. 44–53, XP 002048809.

Szeliski, et al.; "Direct Methods for Visual Scene Recognition" Digital Equipment Corporation, Cambridge Research Lab, pp. 26–33, Jun. 24, 1995.

Krishnan A. et al.; "Panoramic Image Acquisition" Proceedings 1996 IEEE Computer Society Conference on Computer Vision and Pattern Recognition (CAT No. 96CB35909), Proceedings of IEEE Conference on Computer Vision and Pattern Recognition, San Francisco, CA USA 18–20 Jun. 1996.

Dani, et al.; "Automated Assembling of Images: Image Montage Preparation" Department of Electrical Engineering Indian Institute of Technology, pp. 431–445, Oct. 24, 1993.

"Biomarkers of Premalignant Breast Disease and Their Use as Surrogate Endpoints in Clinical Trails of Chemopreventive Agents" *The Breast Journal*, vol. 1, No. 4, pp. 228–235 (1995), Charges W. Boone and Gary J. Kelloff, 8 pages.

"Markovian Analysis of Cervical Cell Images" *The Journal of Histochemistry and Cytochemistry*, vol. 24, No. 1, pp. 138–144 (1976), Normal J. Pressman, 7 pages.

* cited by examiner

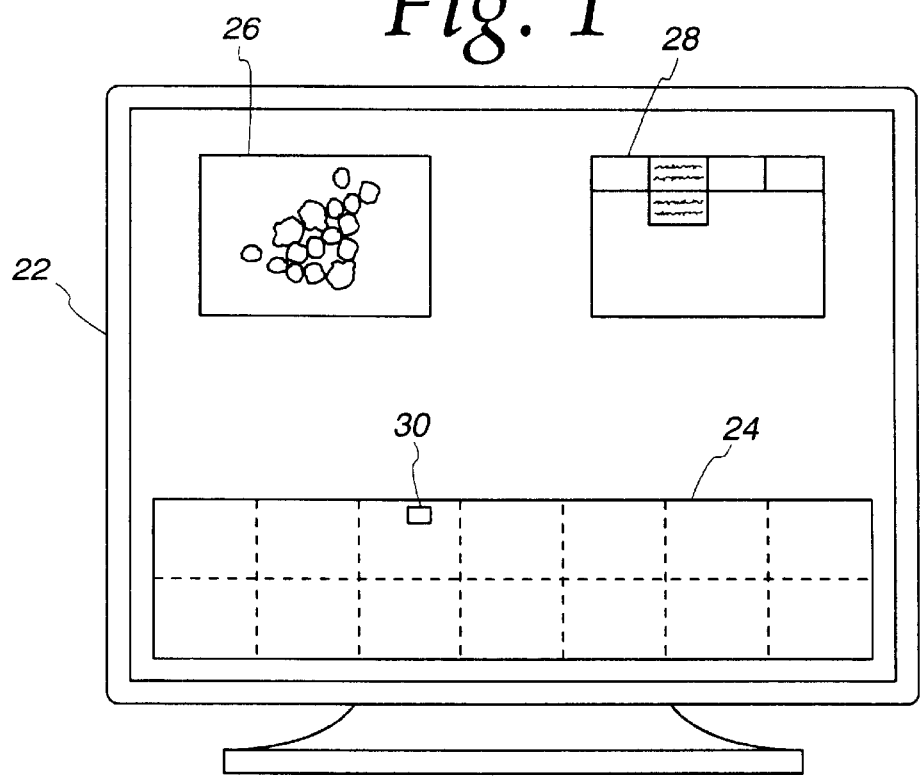
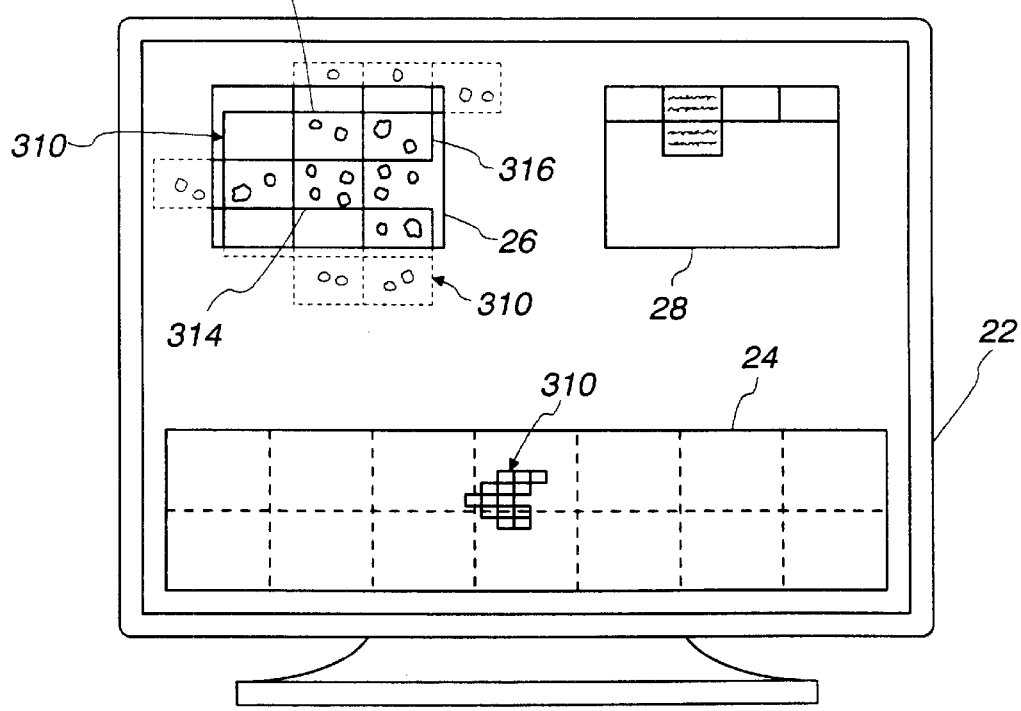

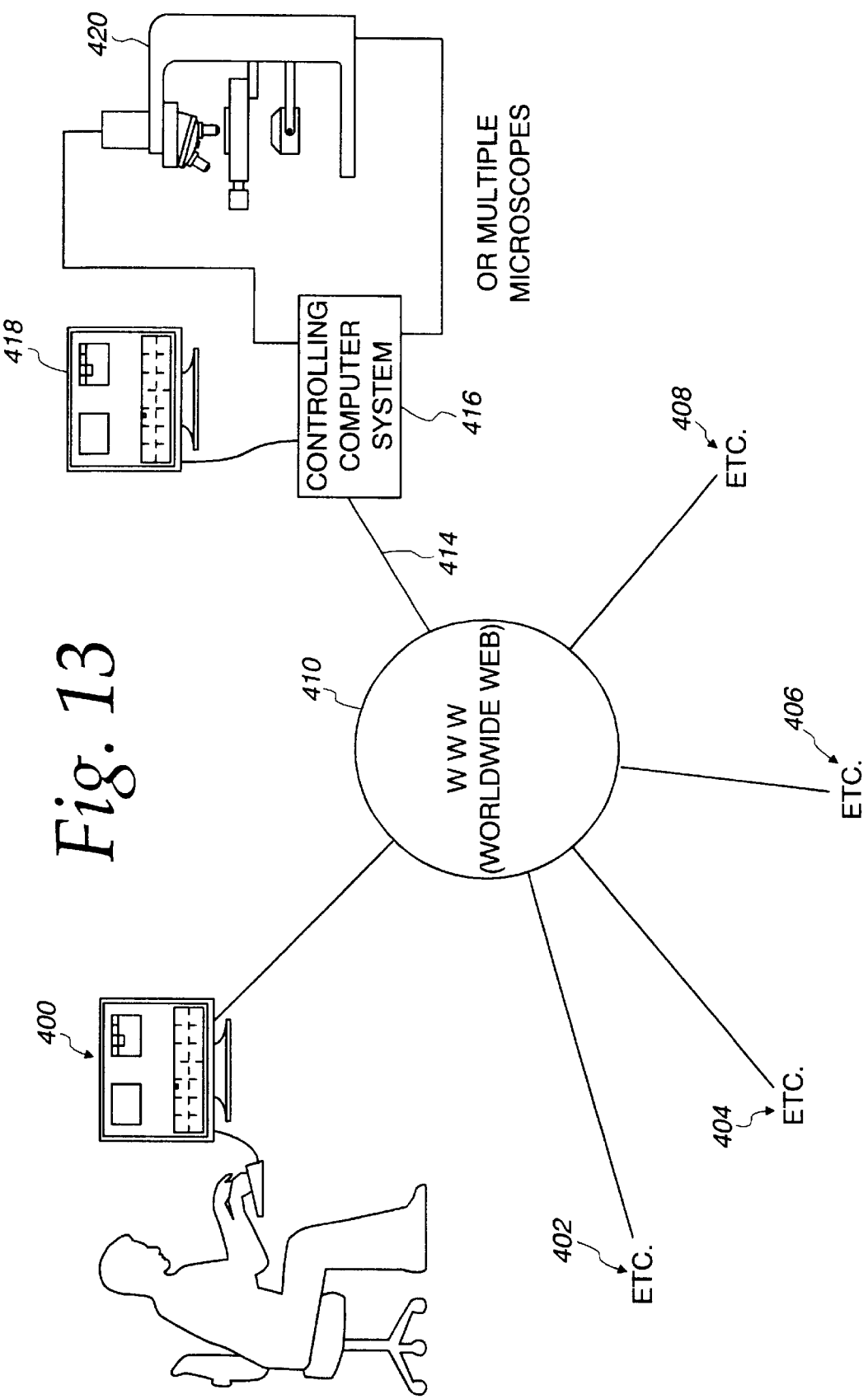

APPARATUS FOR REMOTE CONTROL OF A MICROSCOPE

This is a continuation of a divisional application, U.S. patent application Ser. No. 09/752,022 filed Dec. 28, 2000, now U.S. Pat. No. 6,404,906 which is a divisional application of U.S. patent application Ser. No. 09/395,694, filed Sep. 13, 1999, now U.S. Pat. No. 6,226,392, which is a continuation of U.S. patent application No. 08/805,856, filed Mar. 3, 1997, which is now U.S. Pat. No. 6,101,265, which is a continuation-in-part of U.S. patent application Ser. No. 08/701,974 filed on Aug. 24, 1996, now U.S. Pat. No. 6,031,930.

FIELD OF THE INVENTION

This invention relates to a method of, and an apparatus for, acquiring and constructing tiled digital images from a specimen on a support, such as a microscope slide, and for storing, and transferring the image for viewing by another at a local or remote location.

BACKGROUND OF THE INVENTION

In the image analysis and quantification of DNA from tissue sections as disclosed in U.S. Pat. No. 4,741,031, and also especially in the immunohisto-chemistry assays on the kinds of cell analysis systems disclosed in U.S. Pat. Nos. 5,086,476; 5,202,931; and 5,252,487 issued to Bacus, there is a problem of first locating the cancer regions for analysis under low power and then remembering them when performing the analysis under higher power. Specifically, the problem is that once the microscope is set up for quantification by image analysis under, e.g. 40×, where all of the diaphragms are set and light adjusted, etc., if the operator needs to move to another tissue area, it is first desirable to locate it at e.g. 10×. In fact, often regions can only be located at this power. In order to do so however, all of the settings (diaphragms, light levels, wavelengths of light, etc.) have to be changed to view the tissue at this magnification. Currently, there is no way to ensure that one could go back to the settings at the previous 40× magnification and continue on with the quantitative image analysis of that same specimen. This necessitates finding those areas under 40×, without changing objectives, which is very slow and time-consuming, and often important cancer areas can be missed.

Also, another problem with tissue analysis, at its current state-of-the-art, is that it is not completely automated, for example, with regard to finding structural regions such as glands, basal layers or other important diagnostic regions. However, as set forth in my co-pending patent application Ser. No. 701,974, filed Aug. 23, 1996, if these regions are located, important very sensitive diagnostic measurements can be performed, which patent application is incorporated by reference as if fully reproduced herein. For example, as disclosed in the aforesaid patent application, assays are made of a variety of tissue types, both human and animal for analysis of neoplasia in tissue, for pre-invasive cancer in tissue, and the effects on the tissue of chemopreventive agents. A quantitative analysis by image processing techniques is performed on tissue types, having various architectural features, such as breast tissue, colon tissue, prostate tissue, esophageal tissue, skin tissue, cervix tissue, etc. These tissues have different morphologies, and they undergo different neoplasias usually resulting from a cellular mutation, as may be enhanced by a carcinogen, or resulting from a cellular proliferation rate enhanced by hormones, growth factors, or other inducers of abnormal tissue growth. Often it is desired to quantify small changes in the neoplasia when it is incipient or through a series of analyses performed at close time intervals to measure whether the neoplasia progression is increasing or has been slowed, stopped or regressed.

Usually, the tissue specimens are cut to expose the basal layer for review under the microscope. Typically, the quantitative measurements are performed at 40× to obtain 100 to 400 tissue images. The 40× objective provides a narrow field of view of a very small portion of the entire basal layer. Often, the basal layer is somewhat elongated and generally linear such as a basal layer in a rat esophagus; and the analysis of the basal layer requires examining it along its length. The basal layer in a mouse colon is more in the form of an irregular, circular shape; and the analysis of this basal layer requires traveling about this circular shape. In breast tissue samples, suspected tumor areas may be at widely-spaced points in the stained tissue; and one wants to be able to navigate and travel to these specific suspected areas and to do the 40×analysis at these areas in an efficient manner. There is a need to allow an experienced operator to interact with the analysis to locate and identify such regions in an interactive manner. Especially, an interactive manner that would be familiar and consistent with the use of a microscope manually, with high power magnification and low power magnification simultaneously available, but performed on a computer terminal. Such a level of interaction is different than the interaction with the system disclosed in the above-listed Bacus patents. There is a need to take the level of interaction to a higher level and let each component, the human and the computer, perform the part that it does best, in the most cost-effective manner.

There are available on the market computer-controlled, automated microscopes such as those sold by Carl Zeiss, Inc., Thornwood, N.J., under the name Axioplan 2 for taking photographic images of a specimen in the microscopic field of view. Those particular microscopes have computer-controlled and automatically adjusted subsystems, such as an illumination subsystem, a focusing subsystem, a diaphragm or optical stops subsystem, an objective lens subsystem, or a filtering subsystem. As an operator selects changes from one objective lens, such as one providing low magnification, e.g., 4×, to a higher magnification, e.g., 40×, the computer-automated system will turn the lens turret to switch in the high magnification automatically and adjusts the lens and also automatically adjusts the illumination to eliminate glare and to provide the proper light illumination including light density. Further, the focus is adjusted, and the proper diaphragm openings are automatically reset. Thus, the computer-controlled, automated subsystems automatically reset to values stored and predetermined for each selected objective lens and the analysis being done.

Those particular microscopes can be used to view various objects or specimens, but are most typically used to view and to take still photographs of biological specimens, such as tissues and cells. Those particular microscopes lack a computer-controlled X and Y stage for translating a specimen-carrying slide with respect to the field of view of the selected objective lens. Currently, pathologists and others who use such microscopes want to view the specimen images in full color or in enhanced colors using fluorescent illumination and/or monochromatic images using the automated filter subsystems on the microscopes. Currently trained pathologists or clinicians are accustomed to manually adjust and have a microscope available to them to view larger areas of the specimen at low magnification, and then to momentarily switch in a new higher magnification lens to obtain a more highly magnified image of a portion of the specimen viewed at low magnification. Pathologists and those working in this area have created in themselves a desire to view suspect tissue through a microscope and appear to resist analysis systems that do not provide them this ability.

The microscopic field of view reduces very substantially as the magnification increases. The skill level of the clinician and/or pathologist is important to locate viewing the most suspicious areas or points of interest on the specimen. Sometimes, a technician will do a first assay and analysis. A pathologist will return to the selected points of interest or other points of interest for review and analysis. One concern with respect to a quantitative analysis of breast cancer tissue or prostate biopsy tissue samples to pap smears or other tests for various cancers or the like is that a particularly suspicious point in the tissue may be overlooked and missed during the visual assay or for selection for an automated review analysis. When observing at high magnifications, the field of view is limited to very small area of the specimen. Hence, the observer has difficulty in knowing and remembering the actual, exact location of this small periscopic view within the very large whole specimen.

Often, also the problem is finding or locating the tissue or cells for view at high magnification so that artifacts and/or blank spaces on the slide are not viewed. A number of approaches have been proposed to prescreen and locate by an X and Y address the cells or small points of interest from a very large number of potential points of interest.

There are currently available commercial services for prescreening pap smears where one can mail in slides and the service will do a microscopic prescan at high magnification for suspected or suspicious areas of interest which are marked and given address locations, and also a video tape of the slide specimen is returned by this service to the sender. The sender then reviews the areas of interest located during the prescreening and/or the video tape to complete the analysis.

In an attempt to locate and allow review of specified points of interest, U.S. Pat. No. 5,428,690 to Bacus discloses a system for prescreening of a field of cells on a specimen slide at low magnification before the viewer. When seeing a point of interest to be viewed at high magnification, the viewer will operate a switch or the like to select and record the address of these selected prescreened points of interest. Later, these prescreened points of interest are then brought into position to be analyzed at high magnification. This system is fairly or too slow for many uses.

A very expensive system is currently in use in which a pathologist located at a diagnostic center is able to make a diagnostic opinion with respect to specimens under a microscope at a remote center. The pathologist at the diagnostic center manipulates robotic controls to send telepathy signals via a special, dedicated satellite or other large bandwidth channel to control the microscope at the remote site in approximately real time. The pathologist then can maneuver the remote microscope to shift the microscope's field of view and to send, by telepathy, a highly magnified, very small image back to the pathologist. This system requires each subscriber to have a special microscope operable by manipulation of the robotic controls at the diagnostic center and a dedicated or large bandwidth channel to convey real time video signals and hence results in a very high cost for the assay being done. To assist the pathologist in staying within the specimen at the remote site, a peripheral edge or map of the specimen is made using a second video camera and a light box or by using computerized scanning equipment to trace the outline or peripheral edge of the specimen boundaries. A small circle of light is displayed within the map of the specimen so that the pathologist at the diagnostic center knows the location of the field of view of the highly magnified image within the specimen. In a sense, the pathologist is operating in real time in the same way that he would use his own microscope at his diagnostic center except for a slight transmission delay used to transmit the video signals of the highly magnified image over large bandwidth channel. Although the pathologist has a small map or peripheral outline of the specimen, the pathologist's field of view of the actual specimen is only the small circle of view that is coming through the microscope objective lens. This does not help the pathologist locate suspicious areas of interest as in a prescreening of the entire tissue. The pathologist may switch to the lowest magnification to get the largest field of view of a small section of the specimen, but he never views the entire specimen at any magnification. Also, there is no image analysis quantitative testing from the received images at the diagnostic center; and no quantitative assaying is done with these images at the diagnostic center.

There is a particular interest today in using the Internet system because it is so readily accessible by users at a low cost and using a computer and viewing screen connected to the computer. One problem with trying to do any transmission of digitized, microscopic, highly magnified images over the Internet is that the bandwidth is too narrow to accommodate the tremendous amount of stored data which needs to be transmitted. There is a need for a system which would allow a pathologist or another person, to be able to perform tissue analysis or quantitative assays using a standard computer terminal from a location remote from the automated microscope.

SUMMARY OF THE INVENTION

In accordance with the present invention, a person such as a pathologist at a computer terminal may control an automated microscope to acquire on a computer screen or window images of the specimen at different magnifications as selected by the person. Further, the person may receive on the screen a low magnification, reconstructed image of the entire specimen to aid the person in interactively selecting points of interest on the specimen, such as along a basal layer of a tissue specimen.

More specifically, and in accordance with the present invention, the microscope's small field of view limitation of a specimen is overcome by providing to the viewer a reconstructed, digitized and magnified image of the entire specimen (or a very large portion of the specimen) for performing a visual analysis of the entire tissue in full color to aid in the selection of points of interest to be viewed at a higher magnification. This is achieved by acquiring a large number of low magnification images of the specimen through a microscopic scanning system, e.g., 35 image tiles of the specimen at 1.25x, and then assembling and coordinating the tiles to form an overall, low magnified image of the specimen, i.e., a macro image of the specimen. Preferably, the digitized macro image is reduced in size by a software system to a smaller size, e.g., a ¼ size image that is displayed on a local screen or is sent over a low band width or a high band width channel to a remote screen. Thus, the pathologist not only does not need to have others do a slow laborious prescreening to locate suspicious areas for analysis or for viewing at high magnification, he can use his own experiences to go directly to the most suspicious areas which he sees on the macro image. He can, on a priority basis, do the most suspicious area first, followed by lower priority areas of interest.

In accordance with the present invention, there is provided a new and improved automated, computer-controlled microscope that displays the low magnification composite image of the specimen to allow the user to view and to interactively select points of interest, each of which may be displayed at high magnification. This is achieved by providing the user with a marker, such as a cursor or the like, to select the defined area of interest; and to acquire reproduced, spatially adjacent high magnification, digitized images of the selected area of interest. More specifically, the specimen, when it was first scanned at low magnification to provide a macro view of the specimen, the addresses or locations of the tile images and/or pixels for the composite image were acquired. Therefore, any selected region of interest in the macro image has locations to which the microscopic stage may be automatically repositioned under a changed, higher magnification lens to acquire higher magnification, digitized image tiles that can be assembled into a micro image. Herein, both the macro and micro images are formed of adjacent digitized image tiles which have been coordinated to reproduce spatially the original image that was scanned.

It is the high magnification images, usually at 40×, that were analyzed using image processing techniques as disclosed in the aforesaid patent application, to provide an assay or numerical histological data for the specimen.

In accordance with the preferred embodiment of the invention, the pathologist may select a larger region for analysis at high resolution than can be accommodated at this magnification on his high magnification viewing screen. He can, though, view all of the adjacent, highly magnified, digitized image tiles on this high magnification screen by scrolling up or down or right to left to shift these digitized, adjacent image tiles into view on the screen. Thus, even at a higher magnification of a region the pathologist is able to obtain a much larger view than the small field for the objective lens in use of adjacent tissue or cells to give him a broader, overall perspective of what is happening or what has happened in specific section of a specimen. For instance, a pathologist may want to see at high magnification and to assay at this high magnification, a suspicious area, the pathologist can draw a mark about the area and cause it to then be assayed and displayed.

By having displayed on a low magnification screen or split screen of the full composite area, by having the high magnification region being marked on the low image screen, and by having the region being scrolled to view adjacent high magnification images on the high magnification screen, the pathologist has available information to guide him in the sense of helping to navigate intelligently within the specimen in his search for cancerous tissue or the like for further inspection or measurement of malignant characteristics. Often, when restricted to a field of view of an objective microscope, the pathologist has a difficult time, in the words of a cliche, of seeing the forest for the trees. In the present invention, the pathologist has a full, magnified, reduced in size specimen view with the higher image area marked thereon to guide him and to let him see the forest. He can also see a region of the forest at higher magnification by scrolling adjacent tree images onto the high magnification screen.

In accordance with a further aspect of the invention, the user may elect to change to an intermediate magnification being viewed by either switching automatically to a new objective lens and acquiring new digitized image tiles at the intermediate magnification or by using software to reconstruct from the existing high and low magnification, digitized images a new intermediate digitized image.

The preferred, low magnification image, which is reduced in size, can be transmitted over narrow band width channels such as a local area network or over the Internet through various servers and computers. Likewise, the reconstructed, high magnification images can be transmitted over such narrow band width channels. Because the microscope is fully computer controlled, a pathologist or other person having a split screen computer such as a PC, can be connected to the microscope and operate it from a remote location to obtain the macro image and to navigate to points of interest and obtain the desired micro images. With the present invention, there is no need for a specialized microscope at each remote location nor for a broad band channel to send video signals in real time between the diagnostic center and the remote location.

BRIEF DESCRIPTION OF THE DRAWINGS

FIG. 1 is a screen view of a system embodying the present invention showing a low magnification image of a specimen on a microscope slide in one window, a high magnification image of a portion of the low magnification image selected by a region marker and a control window;

FIG. 2 is a view of a display screen of the apparatus embodying the present invention showing the control window a low magnification window having a plurality of high magnification micro image regions delineated therein and a high magnification window including one or more of the micro image regions;

FIG. 13 is a block diagram of a remote networked system for distributing and accessing diagnostic images and data through a hypertext transport protocol based server directly or over a packet network;

DETAILED DESCRIPTION OF THE PREFERRED EMBODIMENT

Figure 3:
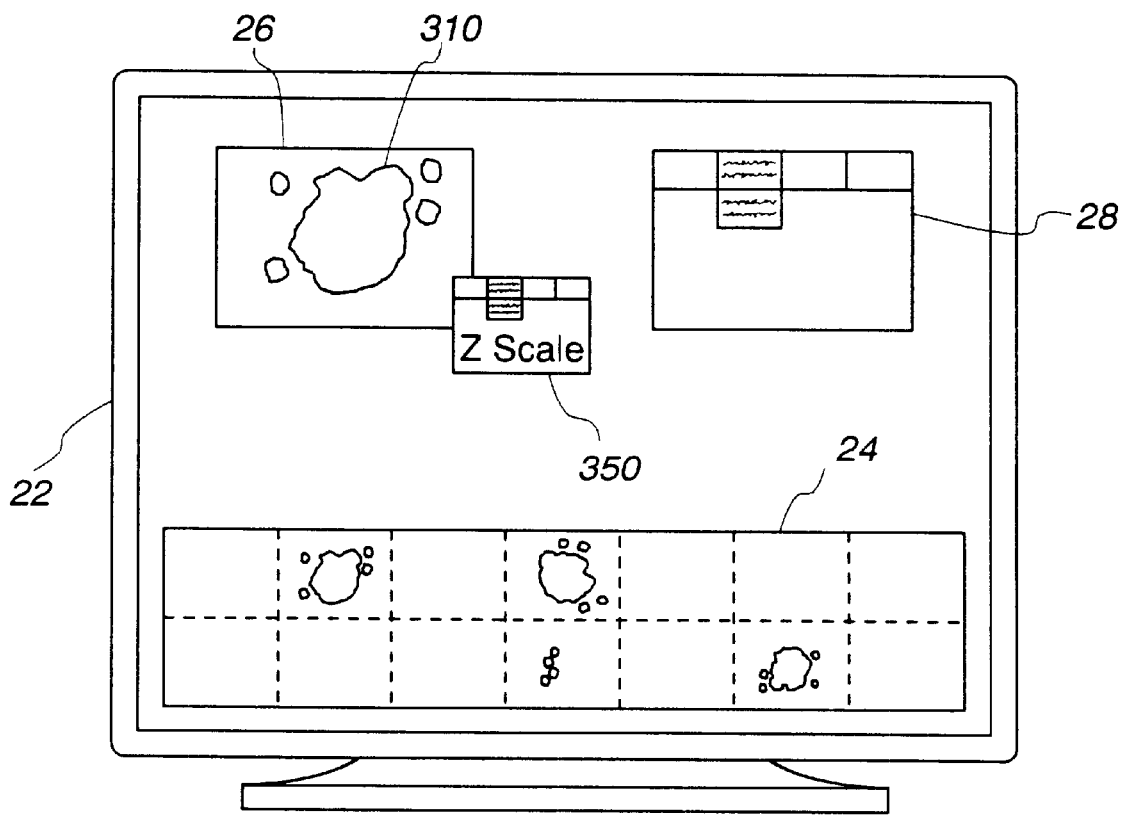
FIG. 3 is a view similar to FIG. 2 including the control window but also including a low magnification region from the slide showing regions marked by a histology grade or structure through automatic analysis of tissue and a high magnification window showing markings related to the grading or histology grade yielded by the automatic analysis of tissue in combination with a window showing a numerical score.
Figure 4A:
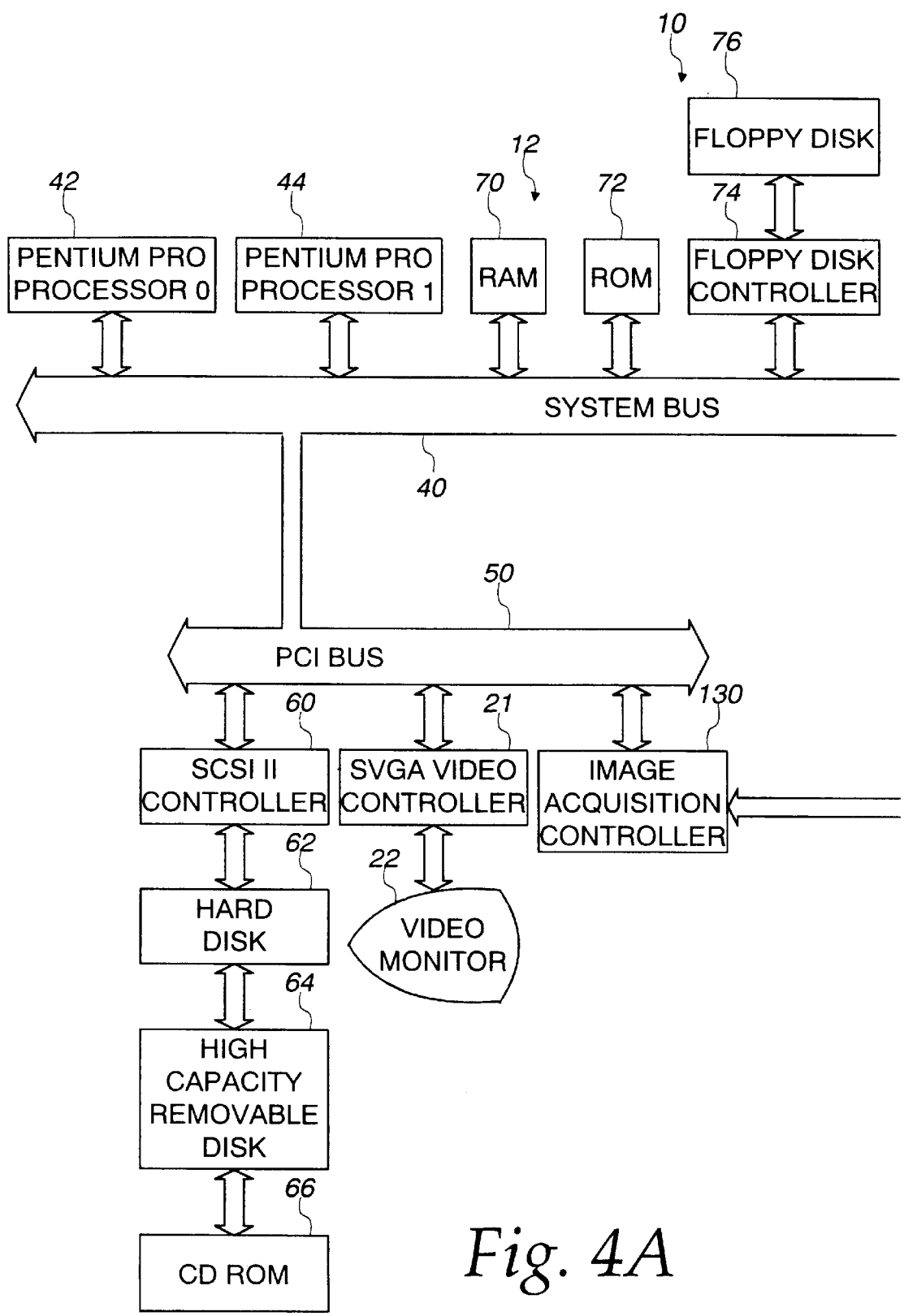
FIGS. 4A and 4B are a block diagrams of the apparatus embodying the present invention.
Figure 4B:
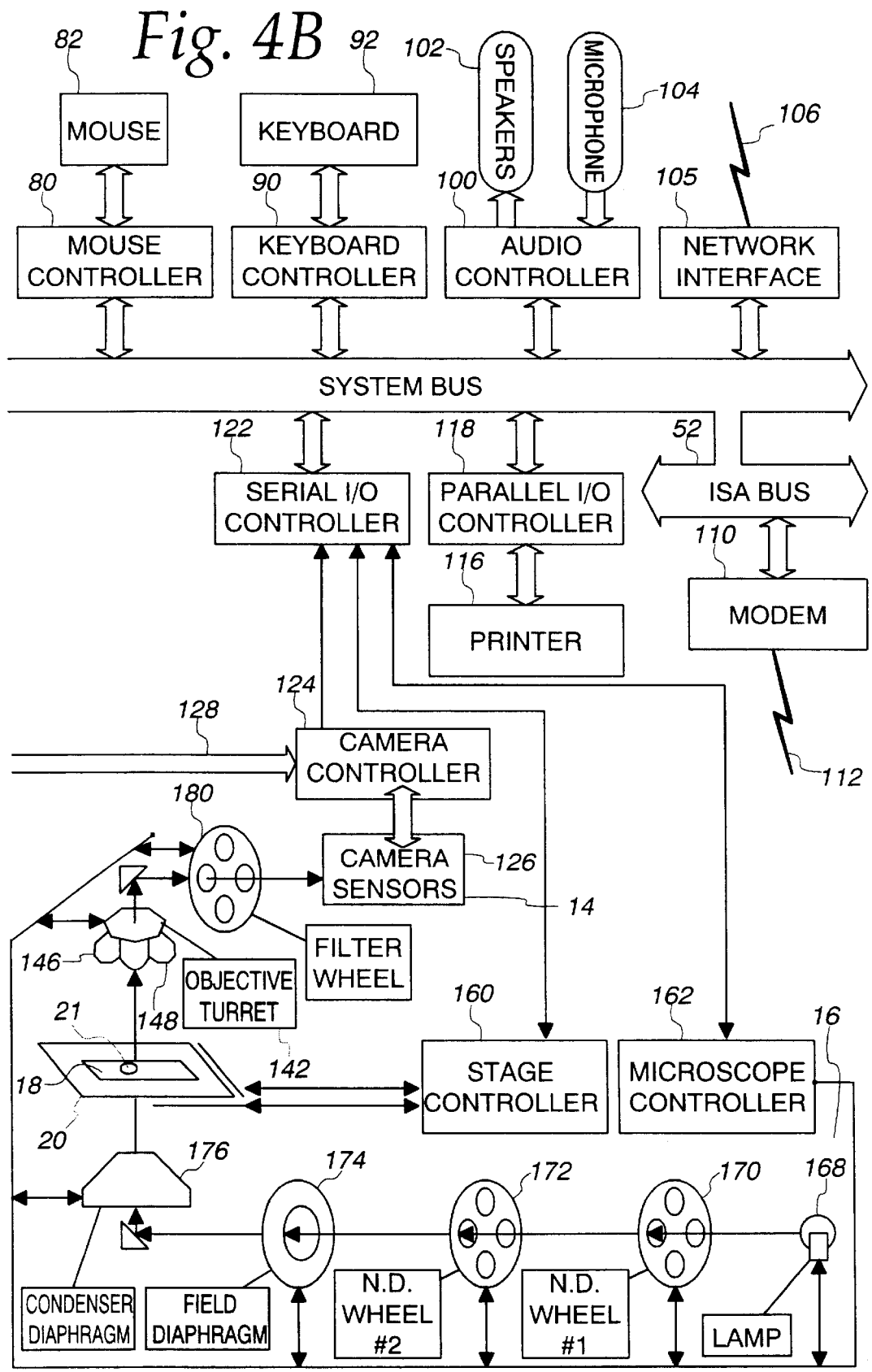
Figure 5:
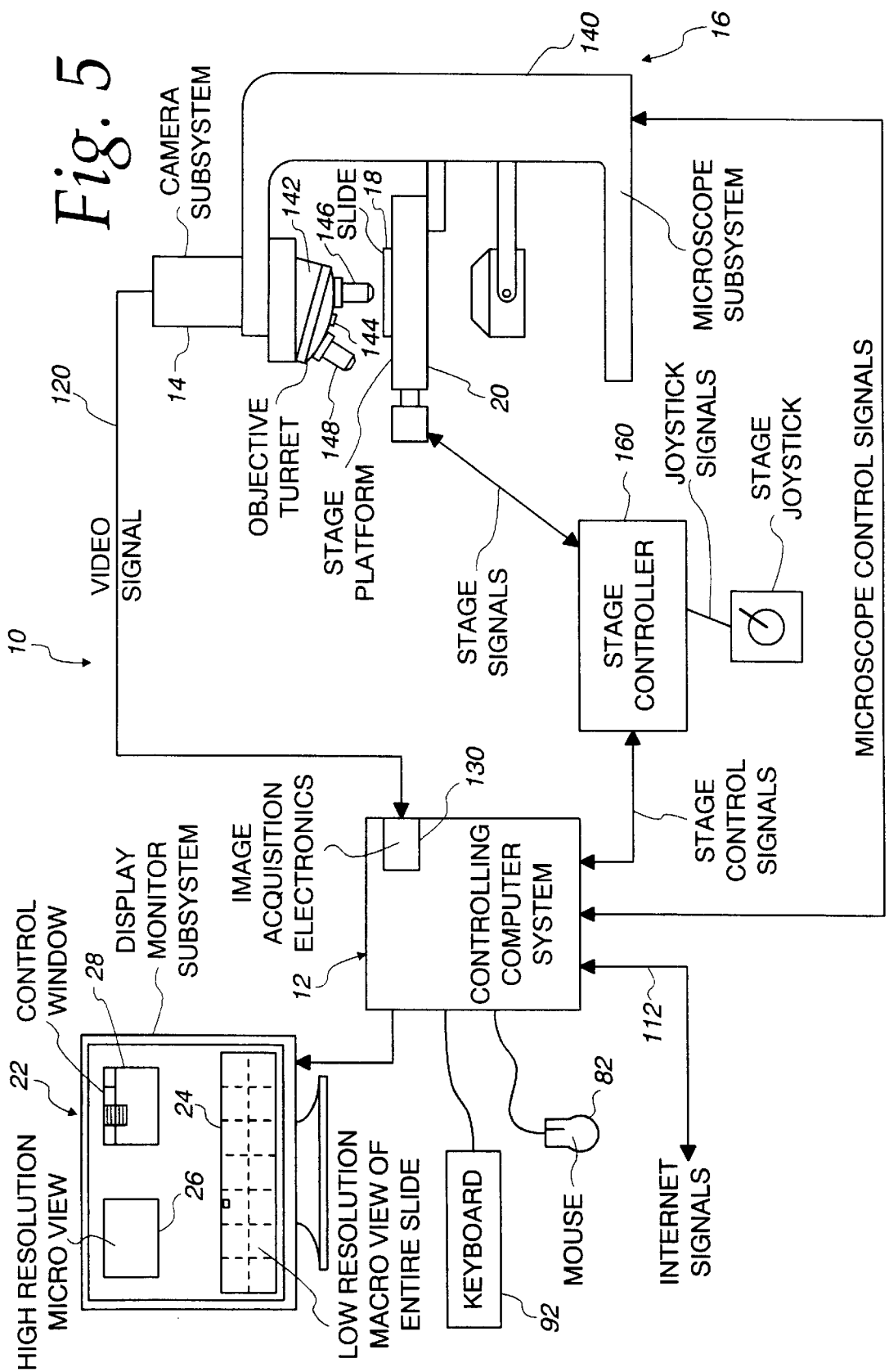
FIG. 5 is a block diagram of a portion of the apparatus shown in FIG. 4 showing details of a mechanical arrangement of a microscope.

Referring now to the drawings, and especially to FIGS. 4 and 5, apparatus for synthesizing low magnification and high magnification microscopic images is shown therein and generally identified by reference numeral 10. The system includes a computer 12 which is a dual Pentium Pro personal computer in combination with a Hitachi HV-C20 video camera 14 associated with a Zeiss Axioplan 2 microscope 16. The computer system 12 is able to receive signals from the camera 14 which captures light from the microscope 16 having a microscope slide 18 positioned on an LUDL encoded motorized stage 20. The encoded motorized stage 20 includes a MAC 2000 stage controller for controlling the stage in response to the computer 12. A microscope slide 18 includes a biological specimen 21 which is to be viewed by the microscope and whose image is to be digitized both at low magnification and at high magnification as selected by a user. The low magnification digitized image is then displayed on a 21 inch Iiyama video display monitor 22 having resolution of 1600 by 1200 to provide display screens of the type shown in FIGS. 1 through 3 including a low magnification image 24, for instance, at 1.25 power, a high magnification image 26, for instance at 40 power and a control window or image 28. The low magnification image may have identified therein a region 30 which is reproduced at high magnification in high magnification screen or window 26 so that a pathologist or other operator of the system can review architectural regions of interest in low magnification image 24 and simultaneously view them in high magnification in the high magnification screen or window 26 to determine whether the cells forming a portion of the architectural feature need be examined further for cancer or the like or not.

The computer 10 is constructed around a PCI system bus 40 and has a first Pentium Pro microprocessor 42 and a second pentium pro microprocessor 44 connected thereto. The system bus 40 has connected to it a PCI bus 50 and an ISA bus 52. The PCI bus 50 has a SCSI controller 60 connected thereto to send and receive information from a hard disk 62. The hard disk 62 also is coupled in daisy chain SCSI fashion to a high capacity removal disk and to a CD Rom drive 66. The hard disks 62 contains the programs for operating the system for controlling the microscope 16 and for processing the images as well as for doing a quantitative analysis of the selected portions of the histological specimens being viewed on the slide 18. The system bus 40 also has connected to it a random access memory 70 within which portions of the program being executed are stored as well as a read only memory 72 for holding a bootstrap loader as well as portions of the basic input/output operating system. A floppy disk controller 74 is coupled to the system bus 40 and has connected to it a floppy disk drive 76 for reading and writing information to a floppy disk as appropriate. A mouse controller 80 is coupled to the system bus and has a mouse 82 which operates as a pointing device for controlling manipulations on the screen 22 and within the windows 24, 26 and 28. A keyboard controller 90 is connected to the system bus and has a keyboard 92 connected thereto. The keyboard 92 may be used to send and receive alpha numeric signals to other portions of the computer. An audio controller 100 has a plurality of speakers 102 and a microphone 104 connected thereto for audio input and output and is coupled to the system bus 40. A network interface, such as a network interface card 104, is connected to the system bus and can provide signals via a channel 106 to other portions of a network or internet to which the system may be connected. Likewise, signals can be sent out of the system through a modem 110 connected to the ISA bus 52 and may be sent via a channel 112, for instance, to the internet. A printer 116 is connected via a parallel I/O controller 118 to the system bus in order to provide printouts as appropriate of screens and other information as it is generated. A serial I/O controller 122 is connected to the system bus and has connected to it a camera controller 124 which is coupled to CCD sensors 126 in the cameras. The CCD sensors 126 supply pixel or image signals representative of what is found on the slide 18 to an Epix pixci image acquisition controller 130 coupled to the PCI bus 50.

The microscope 16 includes a base 140 having a stage 20 positioned thereon as well as an objective turret 142 having a plurality of objectives 144, 146 and 148 thereon. The objective 144, for instance, may be of 1.25×objective. The objective 146 may be a 20×objective. The objective 148 may be a 40×objective. Signals from the camera sensors and controller are supplied over a bus 128 to the image acquisition system where they are digitized and supplied to the PCI bus for storage in RAM or for backing storage on the hard disk 62.

Figure 6:
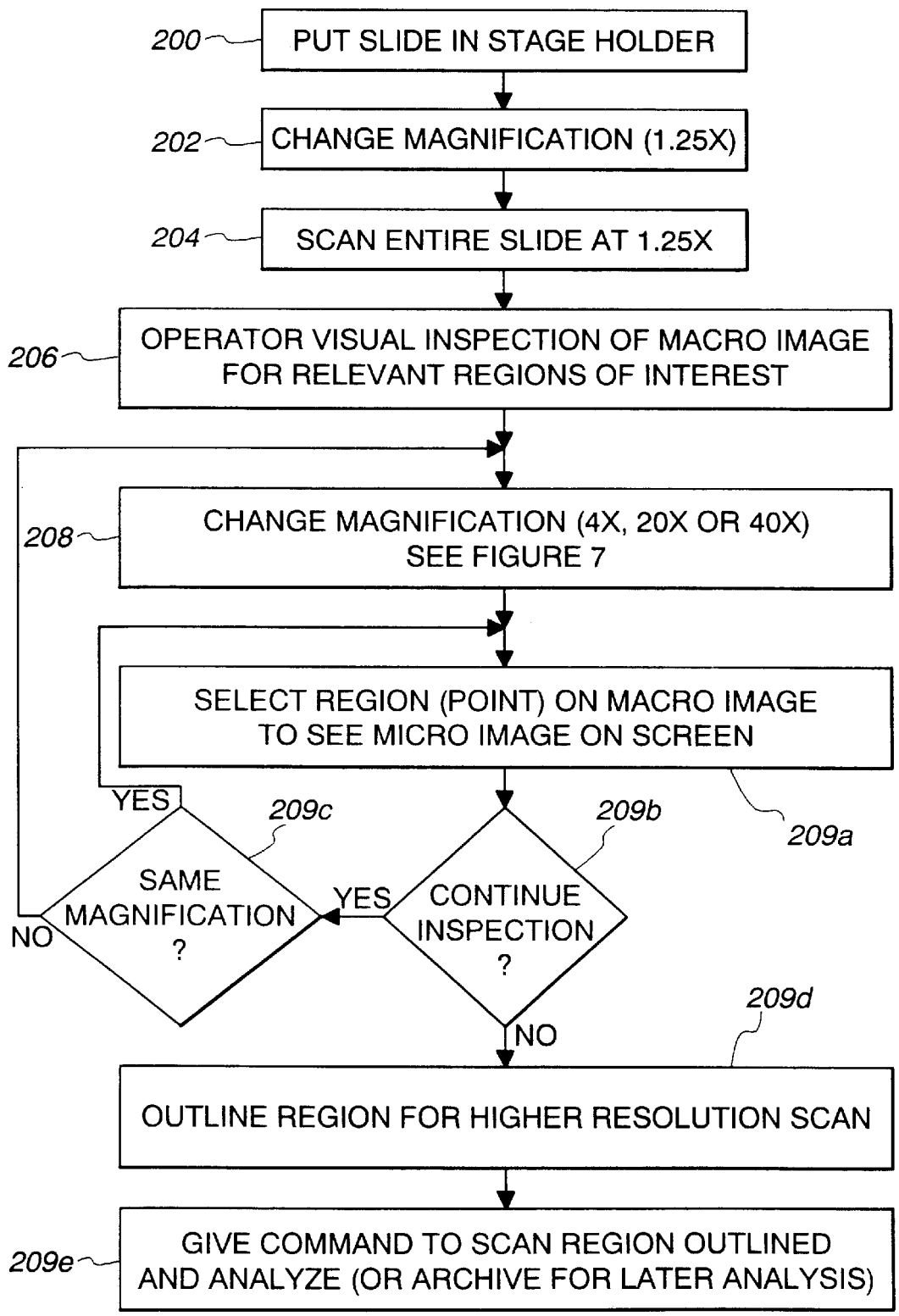
FIG. 6 is a flow diagram related to operation of the apparatus.

When a specimen is on the slide 18 the stage 20 may be manipulated under the control of the computer through a stage controller 160 coupled to the serial I/O controller 122. Likewise, a microscope controller 162 controls aspects of the microscope such as the illumination, the color temperature or spectral output of a lamp 168 and the like. For instance, in normal operation, when a specimen is placed on the slide, specimen slide 18 is placed on the stage 20 in a step 200, as shown in FIG. 6, the processors 42 or 44 send a command through the system bus to cause the serial I/O controller 122 to signal the microscope controller to change magnification to 1.25× in a step 202. This is done by rotating the objective turret of the Axioplan 2 microscope to select the objective 144. Likewise, the controller sets the color temperature of the lamp 168, sets a pair of neutral density filter wheels 170 and 172 and sets a field diaphragm 174 for the correct illumination. A condenser diaphragm 176 is also controlled and a color filter wheel 180 may also be controlled to apply the appropriate filter color to the CCD censors 126 in the camera. The entire slide is then scanned in a step 204. The images are tiled and melded together into the overall image 24 supplied on the screen 22 to provide the operator in the step 206 with a visually inspectable macro image of relevant regions of the slide of interest.

In order to provide the magnified image, the mouse may be moved to identify a marker segment or region which, for instance, may be a rectangular region (as shown as 30 in FIG. 1) which will cause the microscope to change magnification as at step 208 to 4×, 20×, 40×, etc., by rotating the turret to bring the appropriate objective lens system into viewing position.

Next the user, in a step 209a, uses the mouse to select the region on the macro image in order to select the micro image to be viewed on the screen 22. In a step 209b a test is made to determine whether the user has commanded continued inspection. If the user has, a test is made in a step 209c to determine if the magnification is to be changed by changing the selected objective. In the event the magnification is to be changed control is transferred to the step 208. If the magnification is to remain unchanged control is transferred to the step 209a. In the event inspection is not to continue the region selected is outlined for higher magnification scan in a step 209d. In a step 209e, a command may be received to scan or acquire the higher magnification image for display in screen 26. The image may then be archived for later analysis, displayed or analyzed immediately.

In order to perform the magnification called for in step 208, the overall illumination and control of the microscope will be controlled so that in a step 210 the objective turret 142 will be rotated to place the higher power objective above the slide 18. In a step 212 voltage to the lamp will be changed to adjust the lamp 168 to provide the proper illumination and color temperature as predetermined for the selected objective. In a step 214, the condenser diaphragm 176 will have its opening selected as appropriate to provide the proper illumination for that objective. In a step 216, the filter turret 180 will select the proper light wavelength filter to be supplied to the camera sensors. For instance, a red, blue or green filter, as appropriate, particularly if the specimen has been stained. In a step 218 the field diaphragm 174 will have its opening changed. In a step 220 the neutral density filter wheel 170 will select a neutral density filter and in a step 222 the neutral density filter wheel 172 will also select a neutral density filter. In a step 224 the X, Y and Z offsets will be used for reconstruction of the recorded image at the magnification and in a step 226 the current position will be read from encoders in the stage which are accurate to 0.10 micron.

Figure 9:
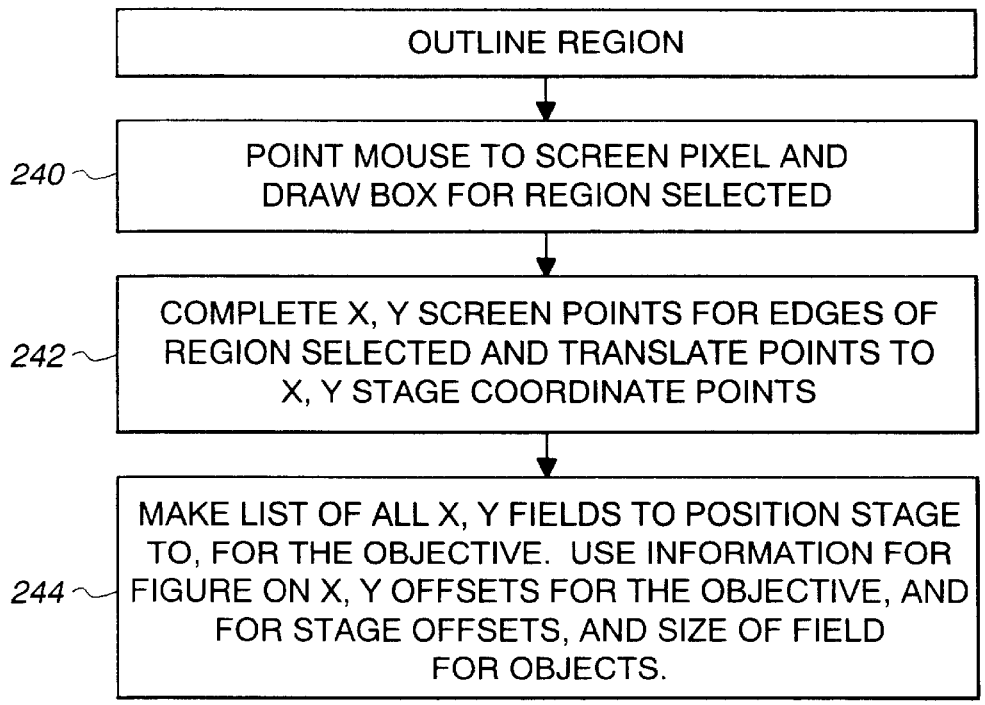
FIG. 9 is a flow chart for a region outlying routine.

In order to identify the selected region the mouse is moved to that area of the region in a pointing operation in a step 240 as shown in FIG. 9. The mouse may be moved to draw a box around the region selected. In a step 242 the X and Y screen points are computed for the edges of the regions selected and the computed image or pixel points are translated to stage coordinate points in order to control the stage of the microscope. In a step 244 a list of all of the X fields for positioning the stage for the objective is stored in random access memory and may be backed up on the hard disk. The information from the X offsets for the objective and the stage offsets is used as well as the size of the field to position the slide properly under the objective to capture the micro image.

Figure 10:
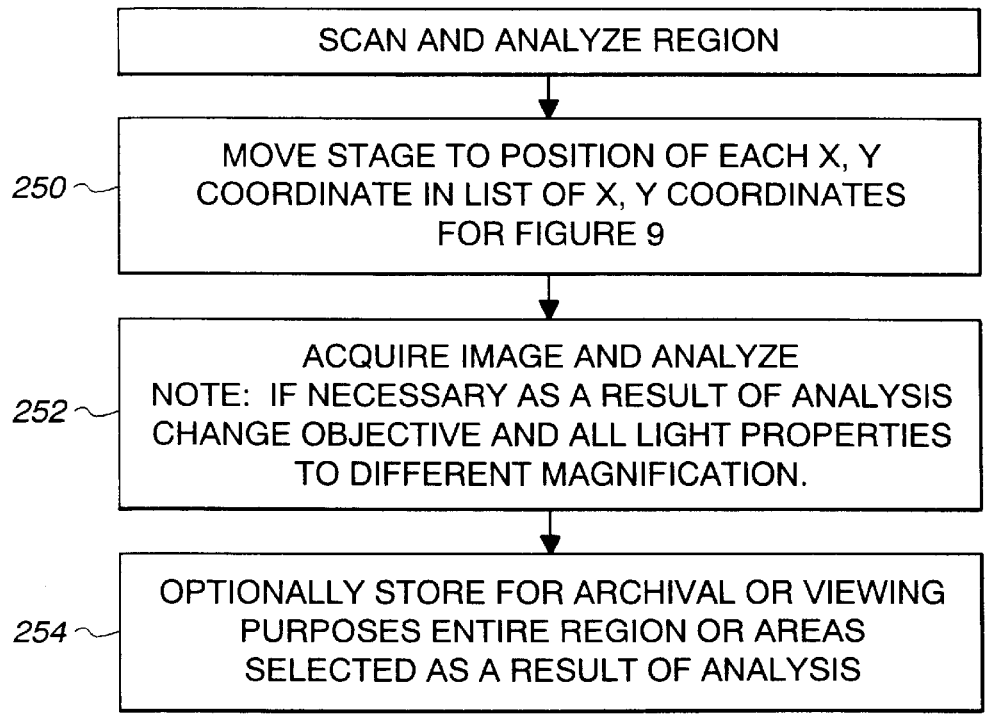
FIG. 10 is a flow chart for a scanning and analyzing routine.

When the slide has been positioned properly, as shown in FIG. 10 in a step 250 the stage is positioned for each of the X and Y coordinate values in stage coordinate values and the digitized image is captured by the cameras and stored in RAM and backed up on the hard disk. The image may be then analyzed quantitatively in various manners such as those set forth in the previously-identified United States application. Optionally the image may be stored for archival purposes in a step 254.

Figure 7:
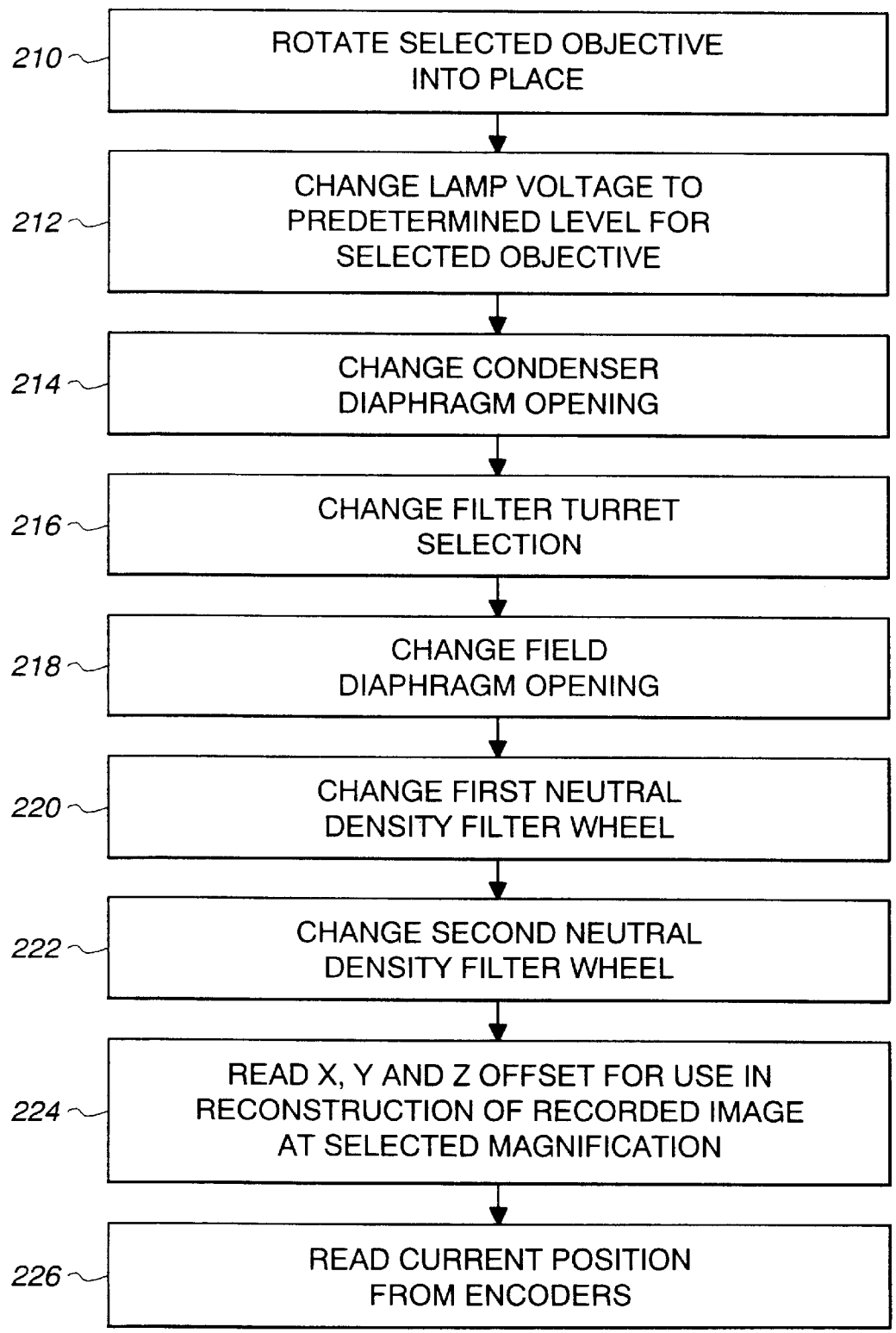
FIG. 7 is a flow diagram of details of one of the steps in FIG. 6.
Figure 8:
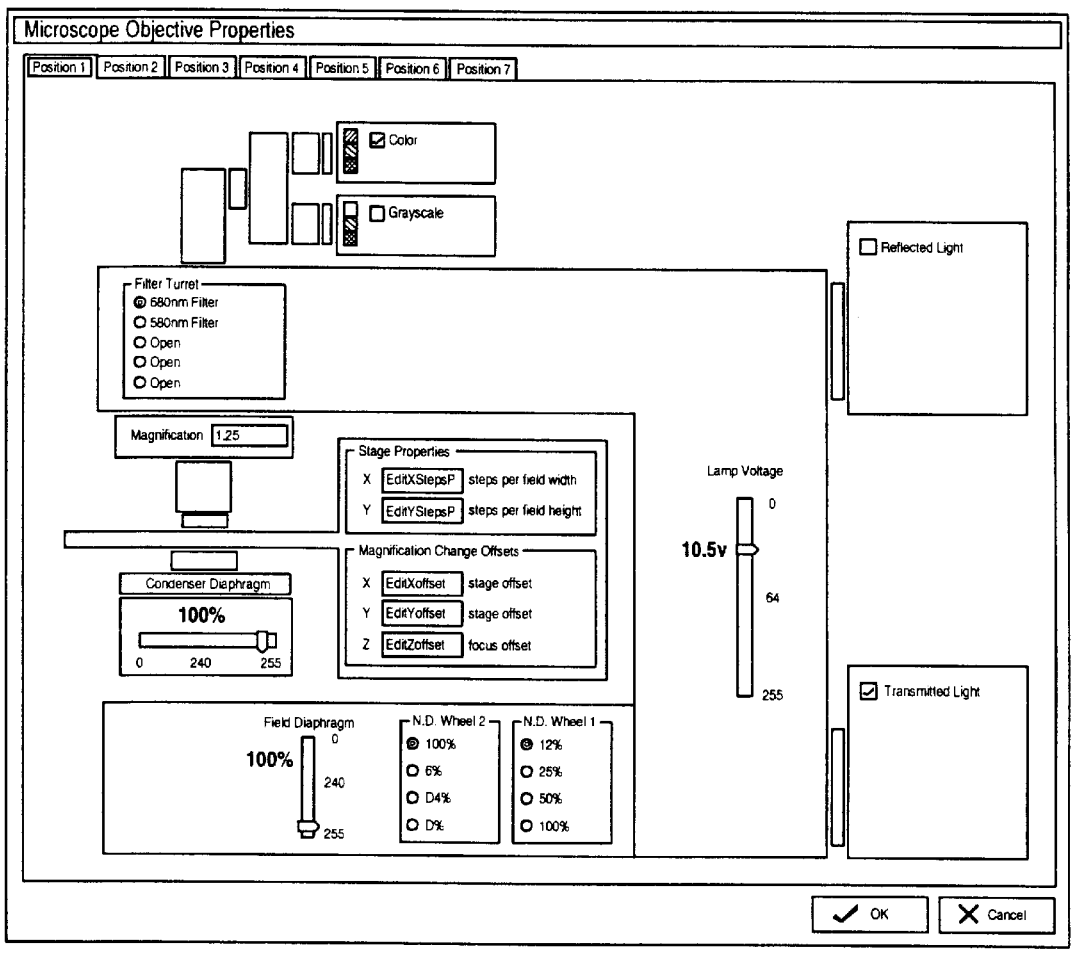
FIG. 8 is a display screen showing control parameters to be manipulated thereon.

In order to override the specific control functions that take place as shown in FIG. 7, a screen is provided as shown in FIG. 8 wherein the X-Y step size can be edited, the X, Y and Z offset can be edited, the lamp voltage can be selected, the neutral density filter can be selected as well as the opening of the field diaphragm and several other microscopic characteristics. FIG. 8 is a view of the settings of the microscope objective properties of the Axioplan 2, computer-controlled microscope.

Figure 11:
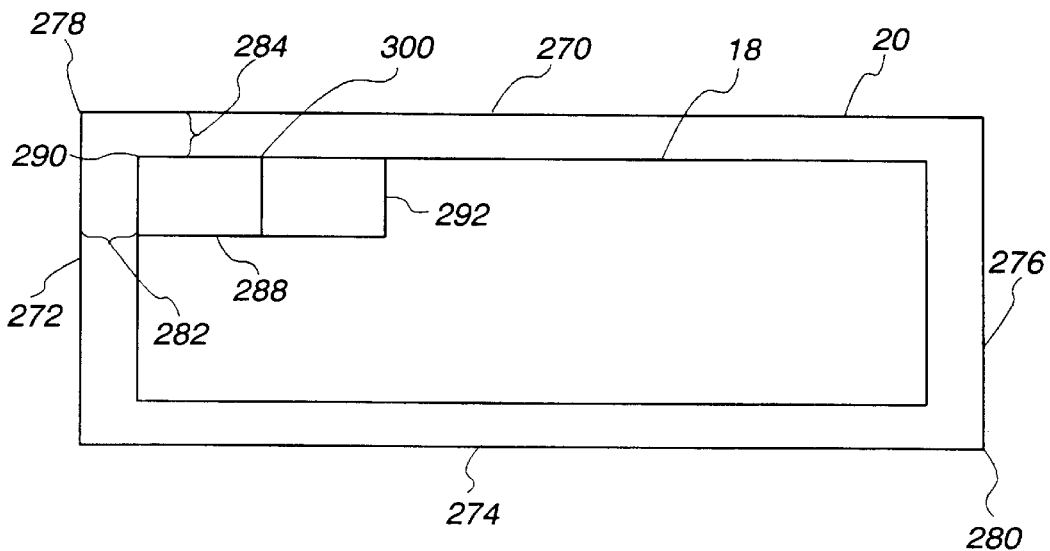
FIG. 11 is a schematic showing of the limits of travel of the microscope stage with respect to the image tiles.

The X and Y positioning is specifically carried out as shown in FIG. 11 where the slide 18 is shown with a slide boundary 270, 272, 274 and 276. Stage boundary for limits of the stage travel for purposes of the stage the stage can be moved all the way from an upper left hand corner of travel 276 to a lower right hand corner of travel 280. At the upper left hand bounded corner of travel 278 limits which a signal that the end of travel has been reached and the stage is then translated a short distance 282 in the extra action and a short distance 284 in the Y direction to define the first tile 288 in terms of a reference point 290 at its upper left hand corner. Since the size of the macro image tile 288 is known, the next macro image tile 292 may be placed contiguous with it by moving the stage appropriately and by measuring the location of the stage from the stage in counters without the necessity of performing any image manipulation. The image tiles 288 and 292 may be abutted without any substantial overlap or they may be overlapped slightly, such as a one pixel with overlap, which is negligible insofar as blurring of any adjacent edges of abutted image tiles. The upper left hand corner 300 of the tile 292 defines the rest of 292 and other tiles can be so defined. Micro image tiles can likewise be defined so that they are contiguous but not substantially overlapping, as would interfere with the composite image. This avoids the problems encountered with having to perform extended computations on digital images in a frame storer or multiple frame storage in order to match or bring the images into contiguity without blurriness at the edges of contiguous image tiles. It may be appreciated as shown in FIG. 2 that the low power image 24 has a plurality of micro images defined therein which are tiled and which are shown in higher magnification as individual tiles 312, 314, 316 and the like in FIG. 2. In addition, the region 310 when magnified as shown in the window 26 may exceed the bounds of the window and thus the window may include scroll bars or other means for allowing the image 310 which is larger than the window 26 to be examined from within the window 26.

Figure 11A:
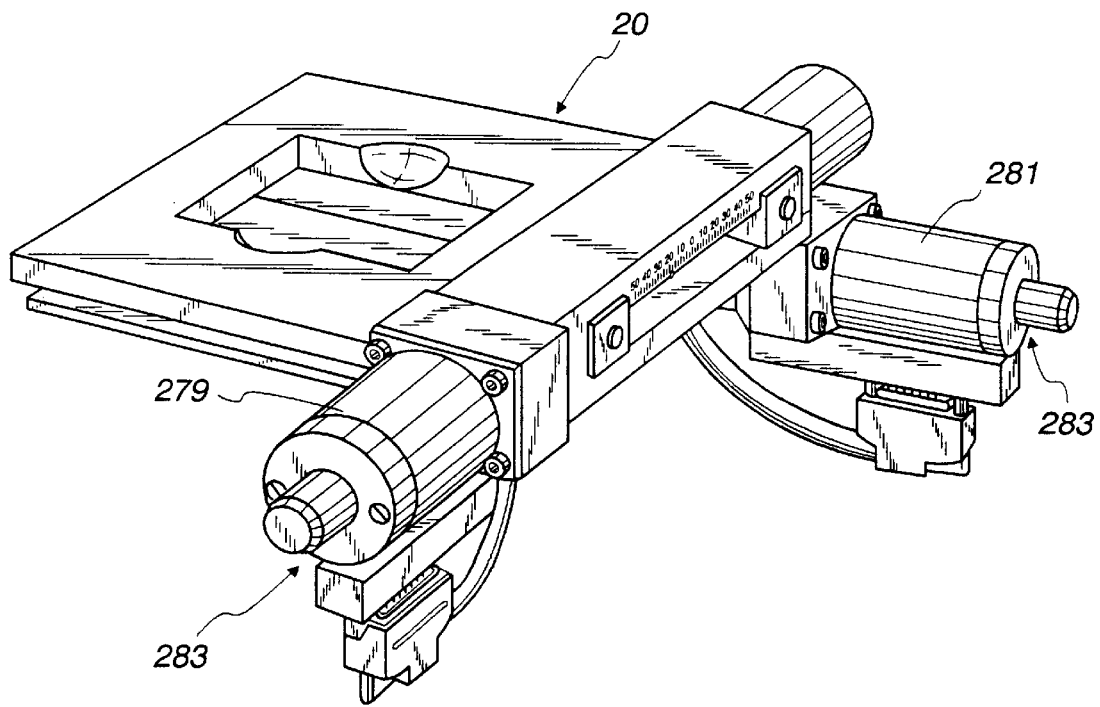
FIG. 11A is a perspective view of the microscope stage and stepper motors and encoders providing a closed loop drive for the motors.
Figure 12:
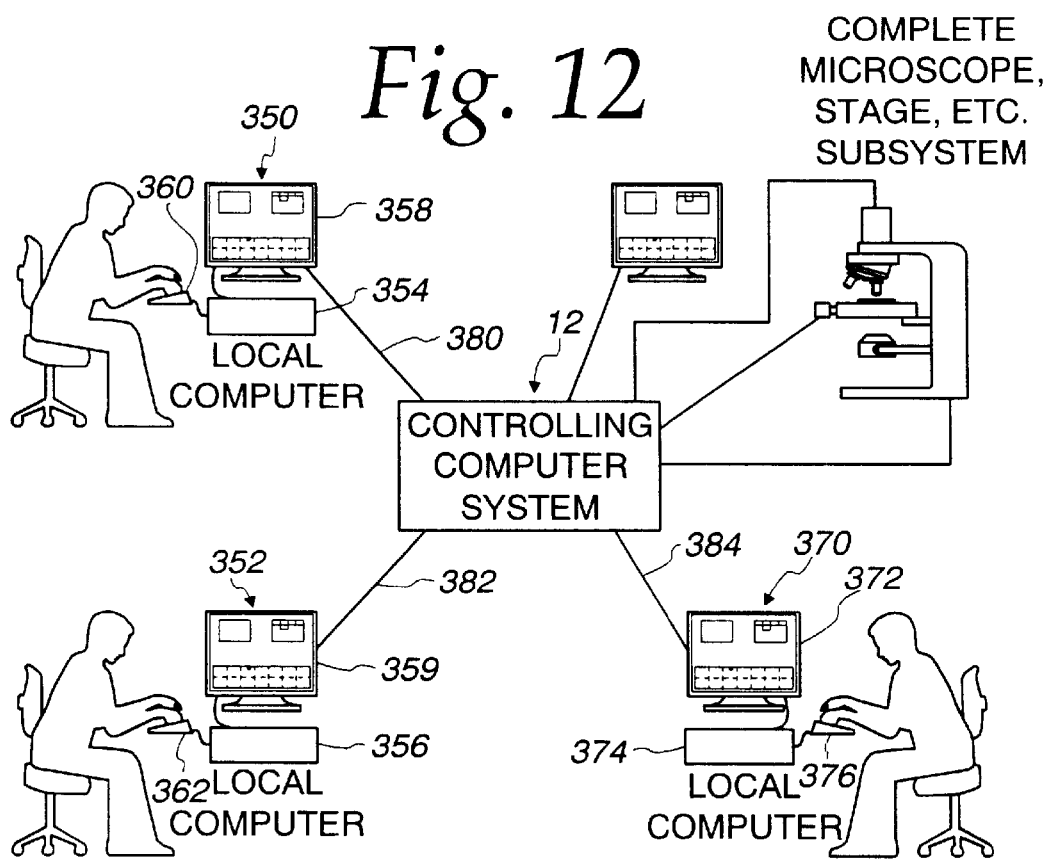
FIG. 12 is a block diagram of a networked system allowing multiple workstations to obtain access to diagnostic image information and to manipulate such information locally at each workstation.
Figure 12A:
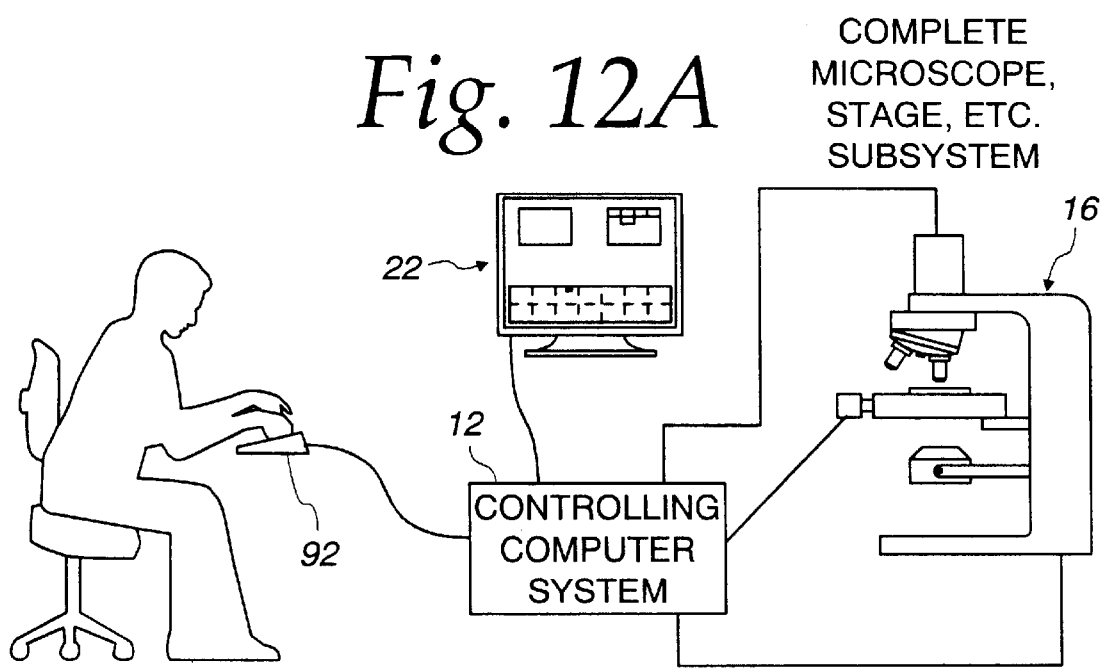
FIG. 12A is a view of the system described in connection with FIG. 5.

The stage 200 is best seen in FIG. 11A and includes the X and Y stepper motors 279 and 281 with their respective encoders, which provide a closed loop system to give the 0.1 micron accuracy versus the usual 5 or 6 micron accuracy of most microscope stages without a closed loop system. This closed loop system and this very high accuracy allow the abutting of the tile images for both high magnification and low magnification images without the substantial overlap and the time-consuming and expensive software currently used to eliminate the overlap and blurriness at the overlapping edges of adjacent image tiles. With the precisely positioned stage and by using the tiling system described in connection with FIG. 11, where the slide is precisely positioned relative to a center point CP for the slide, and the known position of point 278 is always taken from the same point, the tiles may be positioned precisely in a horizontal row and precisely in vertical rows to reconstruct the macro image and the micro image. This reconstruction is done without the use, as in the prior art, of extensive software manipulation to eliminate overlapping image tiles, horizontally or vertically or the haphazard orientation of image tiles.

Furthermore, as shown in FIG. 3, the low power window 24, high power window 26 and control window 28 can be used in conjunction with reporting of quantitative analysis data, histograms, etc. for the specimen being viewed; and such analysis information may be provided as a visual output in a window 320. Each of the various regions 30 that a pathologist may follow in marking various features in the low power window 24 and the high power window 26 may be reflected in both windows in order that an audit trail is provided for the system.

The present invention also includes the facility for allowing remote diagnostics to occur by being able to couple the system either over a network communication facility to an intranet, for instance via the network interface, or via a modem or other suitable connection, to an internet so that once the image has been scanned and stored in memory on hard disks or other storage, remote users may be able to access the low magnification image as well as the high magnification image and move around within both images to make determinations as to the histological characteristics of the samples via Z scores.

An additional feature of the system includes a plurality of networked workstations coupled to a first computer console 12 having a display screen 22 connected to the microscope 14. Satellite work stations 350 and 352 are substantially identical to the work station 12 including respective computers 354 and 356 coupled to displays 358 and 360. The devices can be manipulated through input devices 360 and 362 which may include a keyboard, mouse and the like. Also a third device can be connected including a work station 370, having a display 372, a computer 374 and an input device 376. Each of the devices is connected over respective network lines 380, 382, 384 to the computer 12 which transmission may be via either net or the like. Each of the different operators at the physically separate viewing stations can locate regions from the view of entire tissue cross sections via a macro view and label the regions for subsequent scanning and/or quantitative analysis. A single operator at the instrument station 12 can locate regions to view the entire tissue cross section. Those regions can be labeled for subsequent scanning and/or quantitative analysis with subsequent review and physically remote viewing stations, for instance, in an operating room or in individual pathologists' signout areas in order to review analysis results while still maintaining and reviewing the entire macro view of the tissue and/or the individual stored images from which the quantitative results were obtained. The viewing stations 350, 352 and 370 can comprise desk top computers, laptops, etc. There is no need for a microscope at the network stations 350, 352 and 370.

In a still further alternative embodiment, remote workstations 400, 402, 404, 406 and 408 may be connected through a server 410 which may be supplied via a packet switched network. The server 410 and may be a hypertext transport protocol based server of the type used for the World Wide Web or may be a telnet type server as used previously in internet remote operation applications. The server 410 communicates via a communications channel 414 with a local computer 416 having a display 418 associated therewith, the local computer 416 being connected to the microscope 420. Each of the remote work stations 400, 402, 404, 406 and 408 may perform the same operations as the stations 350, 352 and 370 although they do it from nearby buildings or even from around the world, thus providing additional flexibility for others to make use of the specimen obtained and being viewed under the microscope 420. In addition, stored images may be disseminated through the server 410 to the remote servers 400 through 408 for further analysis and review.

Figure 14:
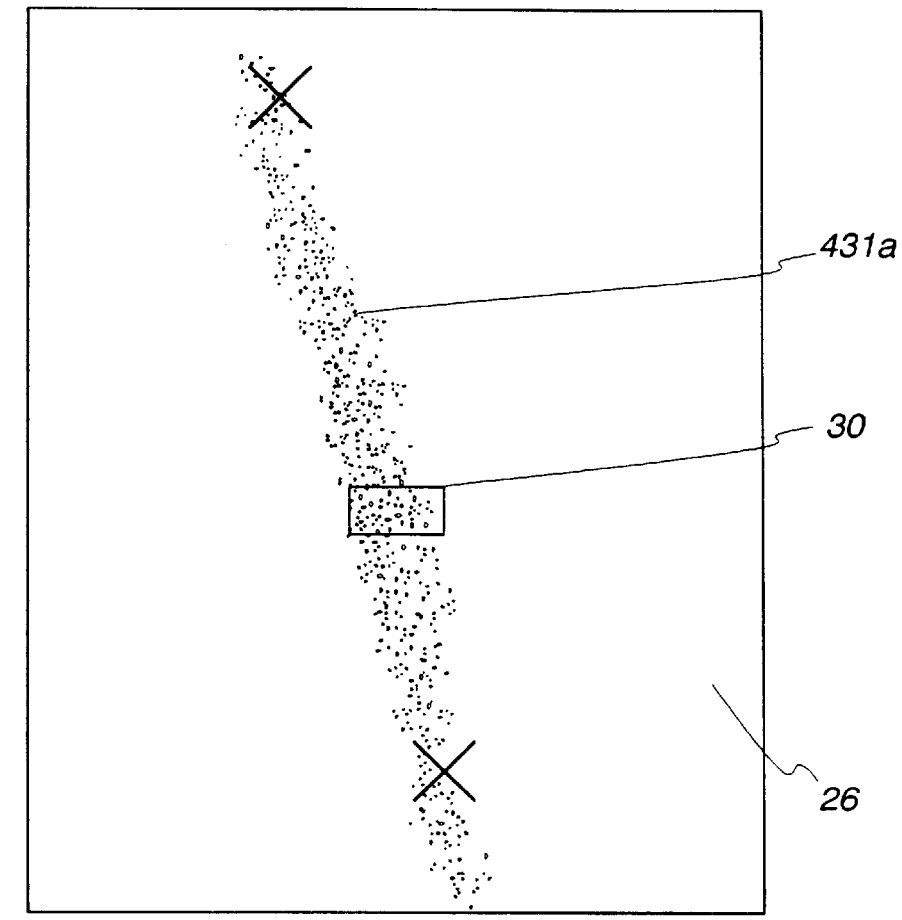
FIG. 14 is a view of a low magnification, reconstructed image from a basal layer of rat esophagus.
Figure 14A:
FIG. 14A is a view of a high magnification, reconstructed image from a selected point of interest from FIG. 14.
Figure 15A:
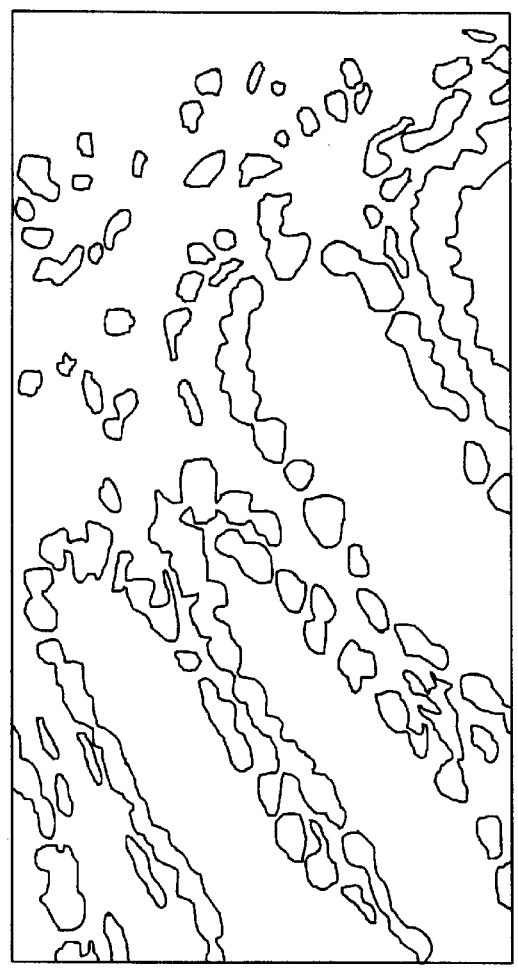
FIG. 15A is a view of a reconstructed macro image of a mouse colon.
Figure 15:
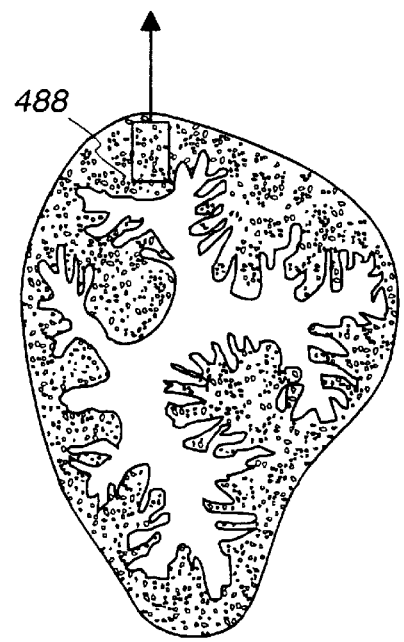
FIG. 15 is a view of a low magnification image of a mouse colon having a basal layer.

In FIG. 14, there is illustrated on screen 28 a basal layer 431a of a cut cross-section of a rat esophagus. The basal layer is elongated and linear in a downward direction, and the selected point of interest is shown as a box 30 on the basal layer on the composite, low magnification image. The high magnification image 26 of this selected point of interest is shown on screen 26 in FIG. 14A. In FIG. 15 is shown a mouse colon as a reconstructed, low magnification macro image 28 which has been reduced $\frac{1}{16}$th in size. The micro image 26 is shown in FIG. 15A, and the marking therefore is shown in FIG. 15.

Figure 16:
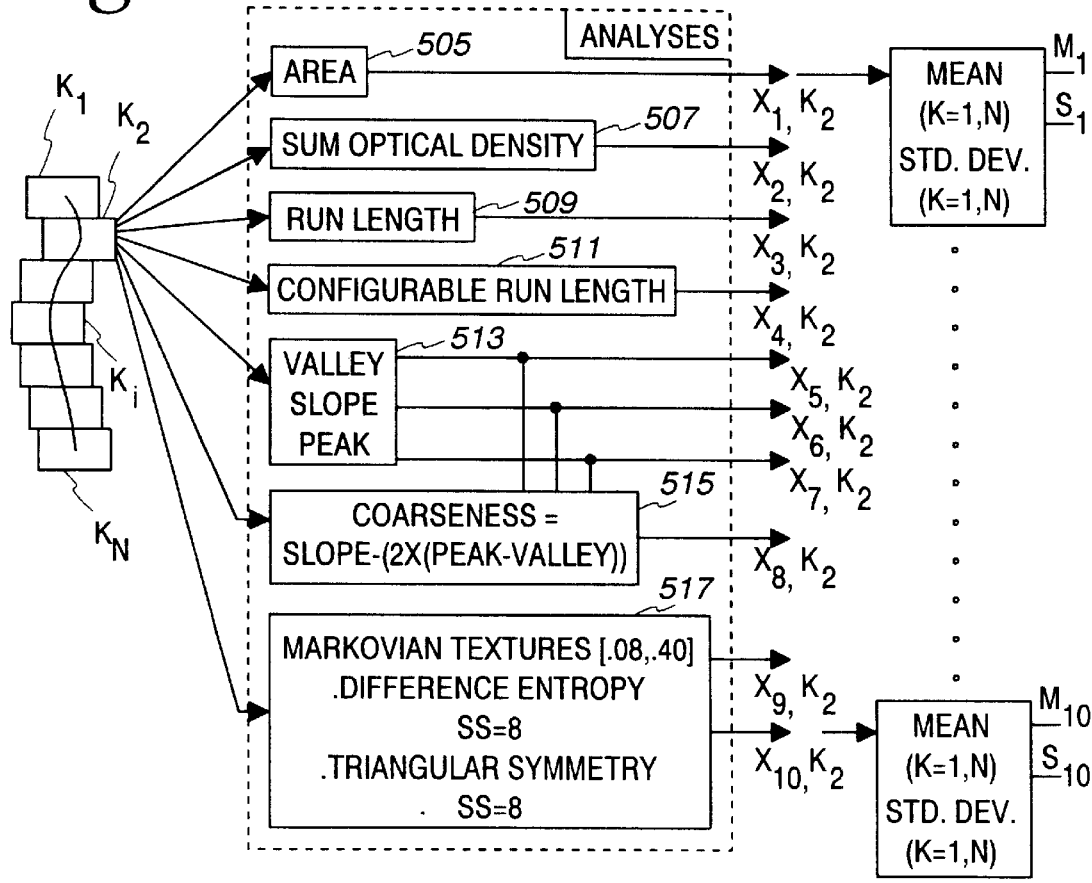
FIG. 16 is a schematic view of an analysis from regions of a basal layer.
Figure 16A:
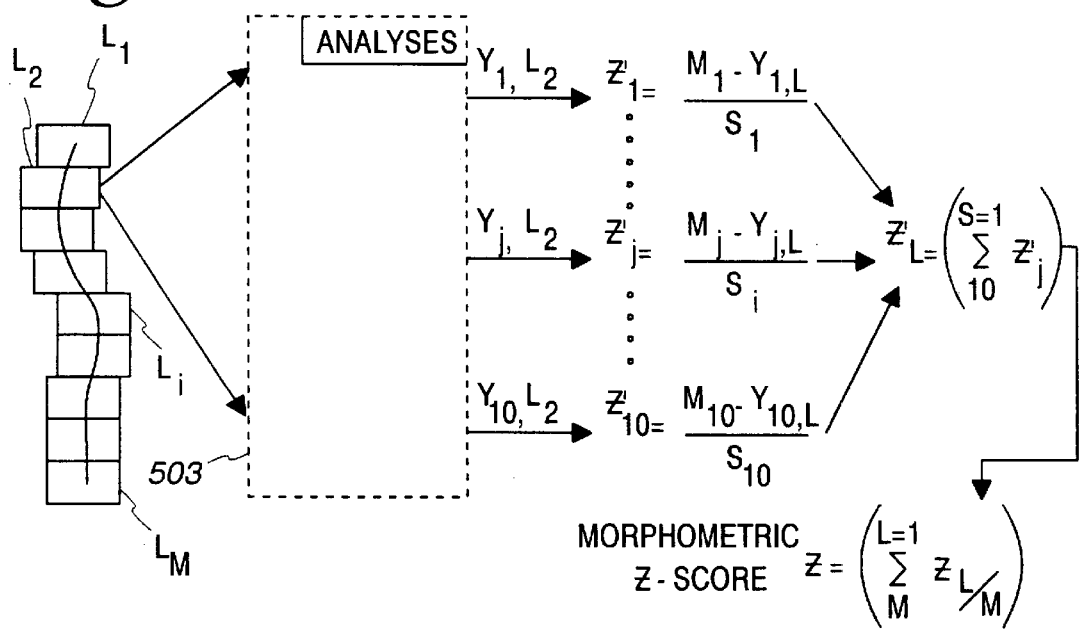
FIG. 16A is a schematic view of an analysis to provide to a Z score.
Figure 17:
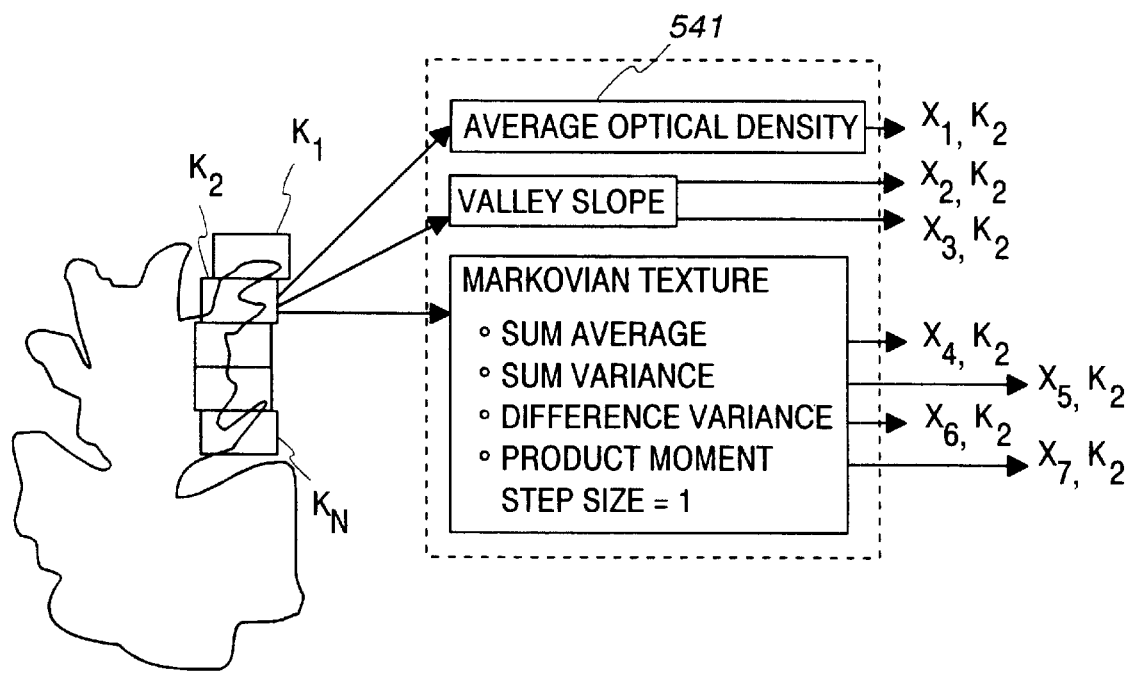
FIG. 17 is a schematic view showing texture analysis tests for regions.

The analysis for texture and for morphological features used to analyze a series of regions 30 on the elongated basal layer that were analyzed at high magnification are shown in FIGS. 16, 16A and 17. The manner of doing these tests and of obtaining a Z score or grade is disclosed in the aforesaid patent application.

While there has been illustrated and described a particular embodiment of the present invention, it will be appreciated that numerous changes and modifications will occur to those skilled in the art, and it is intended in the appended claims to cover all those changes and modifications which followed in the true spirit and scope of the present invention.

What is claimed is:

1. A method of using a computer-controlled microscope imaging system for acquiring an analyzing areas of interest, said method comprising the steps of:

scanning and digitizing a specimen at a low magnification through a microscope at a first location;

displaying to the observer at a remote location the low magnification digitized image of the specimen;

using a computer terminal at a remote location and selecting a segment of the specimen from a displayed low magnification digitized image for viewing at a higher magnification greater than the low magnification;

sending signals from the computer at the remote location over an Internet or Intranet transmission channel for automatically scanning the selected segment at the higher magnification and digitizing a field of view image of the segment;

sending signals representative of the high magnification field of view image over the Internet or Intranet transmission channel to the remote location; and making available at the remote location in real time to the view of the observer the respective, low magnification, digitized image and the high magnification, digitized field of view image of the segment.

2. A method for analyzing biological specimens by an image analysis system having a computer-controlled, automated microscope comprising the following steps:

placing a biological specimen in a microscope at a first location for viewing at a remote location;

connecting a computer terminal at a remote location over an Internet or intranet transmission channel;

using a computer terminal at the remote location to control the image analysis system and microscope at the first location to acquire low magnification, adjacent image tiles of the specimen and to provide a low magnification, composite, macro image from the plurality of image tiles with the series of images being in sensing registration at their respective edges;

displaying at the remote location the macro image on a screen of the computer terminal from a transmission over the transmission channel;

interactively selecting at the remote location at least one point of interest on the displayed macro, specimen image for viewing at a higher magnification;

sending signals from the computer terminal to control and to operate the image analysis system and the computer-controlled microscope at the first location to change objective lenses to acquire a plurality of higher magnification, adjacent image tiles and to provide a high magnification, composite micro image therefrom with the series of images being in sensing registration at their respective edges; and sending signals representative of the higher magnification, image tiles from the first location to the remote location and displaying at the remote location the micro image of the point of interest on the specimen.

3. A method in accordance with claim 2 further comprising analyzing a layer of tissue cells in the specimen for pre-invasive neoplasia.

4. A method in accordance with claim 3 further comprising measuring morphometric features of the specimen and measuring texture features of the specimen from the micro images.

5. A method in accordance with claim 4 wherein interactively selecting at least one point of interest further comprises selecting a series of points along a basal layer of tissue in the specimen for analysis at high magnification.

6. A method in accordance with claim 2 wherein interactively selecting at least one point of interest further comprises:

selecting a plurality of points of interest on the macro image; and recording the location of each selected point of interest.

7. A method in accordance with claim 2 wherein interactively selecting at least one point of interest further comprises:

marking by the remote user of a region on the macro image on the screen that includes portions of adjacent, low magnification image tiles;

acquiring high magnification image tile for each of marked low magnification tiles; and assembling these high magnification image tiles into a micro image and displaying them.

8. A method in accordance with claim 2 including:

simultaneously displaying on computer windows of the computer both micro and macro images of the specimen.

9. A method in accordance with claim 2 wherein the computer terminal is at a remote location from the computer-controlled microscope, and comprising:

first connecting the computer terminal at the remote location over a transmission channel to the image analysis system and the computer-controlled microscope which is located only at the first location.

10. A method for analyzing biological specimens by an image analysis system having a computer-controlled, automated microscope comprising the following steps:

placing a biological specimen in a microscope at a first location for viewing at a remote location;

connecting a remote computer terminal at a remote location over an Internet or Intranet transmission channel;

using the remote computer terminal at the remote location to control the image analysis system and microscope at the first location;

sending signals from the remote computer terminal over the transmission channel to control and to operate the image analysis system and microscope at the first location to acquire a plurality of higher magnification, adjacent, digitized image tiles with the series of images being in registration with each other;

storing the digitized image tiles for use with a server at the first computer terminal; and transmitting by the server from the first location to the remote location and displaying at the remote location images formed from the digitized image tiles transmitted over the transmission channel.

11. A method in accordance with claim 10 comprising:

connecting the server at the first location and the remote computer channel over the Internet transmission channel and sending the stored digitized image tiles over the Internet transmission channel from the first location to the remote location and operating the microscope at the first location by signals transmitted over the Internet transmission channel to the first location.

12. A method in accordance with claim 11 comprising:

providing a consulting pathologist at the remote location for operating the microscope; and sending the digitized image tiles over the Internet transmission and operating the microscope with a live transmission of digitized images tiles within a period of minutes from start of the use of the image analysis system from the remote location.

13. An apparatus for acquiring and transmitting over an Internet or intranet transmission channel a magnified view of a substantial portion of a biological specimen and a higher magnification view of a selected point of interest for viewing at a location remote from the microscope, the apparatus comprising:

an imaging system for acquiring a magnified digitized image of a substantial portion of the biological specimen and including a microscope to acquire a higher magnification, digitized, field of view images for the selected point of interest of the specimen;

a control system at the remote and first locations operable by an operator at the remote location and over the Internet or intranet transmission channel to select a point of interest from the magnified, digitized image of a substantial portion of the biological specimen and causing the image system and microscope to acquire the higher magnification, digitized image for storing in the storing system for a transmitting of the higher magnification image to the remote location;

a storing system for storing data representing the magnified, digitized image as data for transmission over the Internet or intranet transmission channel and for storing data representing the higher magnification image; and a display device at the remote location for displaying the transmitted higher magnification image of the selected point of interest from the transmitted data and for displaying the magnified, digitized image of a substantial portion of the biological specimen from the transmitted data.

14. An apparatus in accordance with claim 13 wherein the imaging system for acquiring a magnified digitized image of a substantial portion of the specimen comprises:

a computer controlled microscope stage system for stepping to acquire a series of adjacent, field of view images taken through the microscope and for registration with one another to provide a composite image of adjacent fields of view larger than a single field of view from the microscope.

15. An apparatus in accordance with claim 14 wherein:
an objective lens being used in the microscope having a lower magnification and resolution than an objective lens being used for the high magnification in order to obtain the low magnification, registered adjacent field of view images comprising the composite image.

16. An apparatus in accordance with claim 14 wherein the display device comprises:
a scrolling feature to allow scrolling into view on the display device higher magnification images of adjacent fields of view.

17. An apparatus in accordance with claim 13 wherein the imaging system including a microscope to acquire a higher magnification, digitized field of view image for the selected point of interest comprises:
a computer controlled microscope stage system movable intermittently in steps when acquiring a series of adjacent fields of view taken through the microscope at the higher magnification and registered with one another to provide a composite image of adjacent fields of view larger than a single field of view for the point of interest.

18. An apparatus in accordance with claim 13 wherein the imaging system comprises an X and Y storage device for storing the locations of the images of each of the fields of view.

19. An apparatus in accordance with claim 13 wherein the display device comprises:
a device operable for switching back and forth between digitized higher magnification images at several different magnifications for the same point of interest.

20. An apparatus in accordance with claim 13 wherein the display device includes a monitor having a first portion for displaying the low magnification composite image and a second portion for displaying simultaneously the higher magnification image.

21. An apparatus in accordance with claim 13 comprising:
a marker on the display device movable by the operator to navigate along to composite low magnification image to select a suspect area for viewing by the operator on a subsequent display on the display device.

22. An apparatus for acquiring and transmitting over the Internet magnified microscopic views from a remotely operated microscope, the apparatus comprising:
an image analysis system including a computer controlled microscope for receiving a biological specimen thereon and for acquiring field of view images at different magnifications of the specimen;
a remote computer terminal at a remote location for connection over the Internet to the image analysis system and for operating the image analysis system from the remote location to acquire a high magnification field of view image from the specimen;
a storage device for storing a digitized image of a high magnification field of view as data for transmission;
a server associate with the image analysis system and storage device for transmission of the data to the remote location; and
a display device at the remote location for displaying a low magnification image showing the morphology of the specimen for navigation thereon by the operator when remotely controlling the microscope to select a point of interest and to acquire and transmit a high magnification field of view image of the selected point of interest.

23. An apparatus in accordance with claim 22 comprising:
objective lens in the microscope being positioned to provide multiple magnification images at magnification greater than that used for the low magnification image.

24. A method of performing a quantitative analysis on stored, digitized views of an optically magnified specimen comprising:
storing a plurality of digitized image optically magnified to allow a view of a region and to allow a quantitative measurement thereof a region larger than a single field of view;
selecting a first region of interest from a composite digitized image of at least a portion of the specimen;
performing a quantitative analysis on a digitized image from the first region of interest;
requesting a second stored digitized image from a second region of interest for analysis;
receiving a stored digitized image from the second region of interest;
performing the same quantitative analysis on the stored digitized image front the second region of interest thereby providing a quantitative analysis with respect to the region of interest; and
providing a lower magnification composite view of the specimen to a user to enable the selection of a region of interest for quantitative analysis which is done on a higher magnification and resolution image.

25. A method in accordance with claim 24 comprising:
storing the digitized images at a first location; and
transmitting the stored digitized images to a plurality of other locations to allow simultaneous quantitative analysis to be performed on the same region of interest.

26. A method in accordance with claim 24 comprising:
providing an Internet transmission channel and a server for distribution of the stored displayed images over the transmission channel.

27. A method in accordance with claim 24 comprising:
transmitting the selected digitized images over the Internet to a user.

28. A method in accordance with claim 27 comprising:
a plurality of users accessing the stored, digitized images and a plurality of users receiving their respectively selected digitized images of their respectively selected region of interest for the quantitative analysis.

29. A method of quantitative analysis of a biological specimen comprising:
providing scanned and stored data of optically magnified digitized images from the biological specimen at a first location;
providing an analysis program at a second location physically removed from the first location for performing a quantitative analysis on an optically magnified image;
retrieving data of scanned and stored images upon a request from the first location for transfer to the second request location;
transferring the data for the digitized images to thin second location and storing the retrieved data for optically magnified, digitized images at the second location;
displaying to an observer at the second location a comprehensive image of the specimen formed from the retrieved data;
selecting by the observer of a region of interest from the specimen from the comprehensive view on which to perform the quantitative analysis; and using the analysis program to perform a quantitative analysis on successive, optical magnified adjacent images from the specimen comprising the region of interest obtained from the retrieved data stored at the second location.

30. A method of analysis of a biological specimen on a microscopic slide comprising:

storing a first digitized overall image larger than a single field of view and formed of adjacent fields of view to provide an optically magnified view at a first magnification of a biological specimen on a microscope slide;

storing a second digitized image of optically of a magnified view from the biological specimen at a higher magnification than the first magnification;

viewing the overall image and selecting therefrom a region of interest tot quantitative analysis from the overall image;

retrieving from storage a selected higher magnification, digitized image for analysis; and using the selected high magnification digitized image to conduct a quantitative analysis of the selected region of interest.

31. A method in accordance with claim 30 comprising:

retrieving from storage, a plurality of adjacent, higher magnification images comprising the selected region of interest; and using these higher magnification, retrieved images to conduct quantitative analysis of the selected region of interest.

32. A method in accordance with claim 30 wherein the selected region comprises:

Multiple, adjacent fields of view of the specimen at the higher magnification.

33. A method in accordance with claim 30 comprising:

strolling to shift into view an adjacent high magnification image for viewing by the viewer.

34. A method in accordance with claim 30 wherein the viewer selects a suspicious morphological feature displayed in the overall composite image and navigates therealong when selecting the region of interest to be analyzed.

35. A method in accordance with claim 30 comprising:

displaying simultaneously both the overall image and the higher magnification image; and displaying a location mark on the overall image to located thereon the region of interest.

36. A method in accordance with claim 30 wherein the retrieving from storage comprises:

sending stored data for the digitized, optically magnified image from a first location over the Internet to a remote location; and the selecting of the region of interest comprises sending a request over the Internet from a remote location for a selected higher magnification image to be sent from the first location to the remote location over the Internet.

37. A method in accordance with claim 30 wherein the providing of the stored digitized image comprises:

scanning a biological specimen at a first magnification for the composite images; and scanning the biological specimen a second time at a second higher magnification for the higher magnifications digitized images.

38. A method of viewing suspicious regions of a biological specimen on a microscopic slide for analysis comprising:

providing stored data for a digitized optically magnified overall image of the specimen;

providing stored data for digitized images of the specimen at a higher optical magnification than that of the overall image;

retrieving from storage an overall image of the specimen;

viewing the overall image and intelligently navigating therein to select a region of interest for analysis at higher magnification;

marking on the overall image a selected region for analysis at higher magnification;

retrieving from storage higher magnification images of the selected region of interest; and displaying a higher magnification image of the region for viewing and analysis.

39. A method in accordance with claim 38 compromising storing the stored data for the optically magnified overall image and the higher magnification image on a hard disk;

retrieving the stored data from the hard disk; and displaying simultaneously to a viewer both the optically magnified overall image and the higher magnification images of the selected region of interest.

40. A method in accordance with claim 39, wherein the stored data is at a location remote from the viewing location and the stored data is sent over a communication channel useable by a plurality at users.

41. A method in accordance with claim 40 wherein the common communication channel is the Internet.

42. A method of analysis using a virtual microscope slide comprising:

providing the biological specimen on a microscope slide;

optically magnifying the biological specimen and providing a magnified image:

digitizing the magnified image to provide the virtual microscope slide;

digitally storing the virtual microscope slide to provide a stored virtual microscope slide image of the specimen;

viewing morphological features on the stored virtual microscope slide image;

selecting a region of morphological interest on the retrieved virtual microscope slide image;

retrieving from storage a plurality of adjacent, higher magnification images of the region of interest; and using the retrieved image high magnification images to conduct an analysis of the morphological feature for the biological specimen.

43. A method in accordance with claim 42 comprising:

sending the stored, digitized image over the Internet to provide a virtual microscope slide image for analysis at a remote location.

44. A method in accordance with claim 42 comprising:

retrieving from storage higher magnification images at different magnifications of the region of morphological interest to allow analysis of a morphological feature at different resolutions.

45. A method in accordance with claim 42, comprising:

displaying images simultaneously of adjacent, higher magnification fields of view for the specimen.

* * * * *

UNITED STATES PATENT AND TRADEMARK OFFICE
CERTIFICATE OF CORRECTION

PATENT NO. : 6,674,884 B2
DATED : January 6, 2004
INVENTOR(S) : Bacus et al.

It is certified that error appears in the above-identified patent and that said Letters Patent is hereby corrected as shown below:

<u>Title page,</u>
Item [63], Related U.S. Application Data, Replace paragraph as follows:
-- Continuation of application No. 09/752,022, filed on Dec. 28, 2000, now Pat. No. 6,404,906, which is a division of application No. 09/395,694, filed on September 13, 1999, now Pat. No. 6,226,392, which is a continuation of application No. 08/805,856, filed on Mar. 3, 1997, now Pat. No. 6,101,265, which is a continuation-in-part of application No. 08/701,974, filed on August 23, 1996, now Pat. No. 6,031,930. --

<u>Column 12,</u>
Line 49, after "segment" insert -- simultaneously --;

<u>Column 14,</u>
Line 46, after "for" delete "a";

<u>Column 15,</u>
Line 57, change "associate" to -- associated --;

<u>Column 16,</u>
Line 8, change "image" to -- images --;
Line 22, change "front" to -- from --;

UNITED STATES PATENT AND TRADEMARK OFFICE
CERTIFICATE OF CORRECTION

PATENT NO. : 6,674,884 B2
DATED : January 6, 2004
INVENTOR(S) : Bacus et al.

It is certified that error appears in the above-identified patent and that said Letters Patent is hereby corrected as shown below:

Column 17,
Line 13, change "optically of a" to -- a optically --;
Line 17, change "tot" to -- for --;
Line 33, change "Multiple" to -- multiple --;
Line 36, change "strolling" to -- scrolling --; and
Line 51, change "image" to -- images --.

Signed and Sealed this

Twenty-fifth Day of May, 2004

JON W. DUDAS
*Acting Director of the United States Patent and Trademark Office*